United States Patent [19]

Mjalli et al.

[11] Patent Number: 6,107,274
[45] Date of Patent: Aug. 22, 2000

[54] PIPERAZINES AS INHIBITORS OF FRUCTOSE-1,6-BISPHOSPHATASE (FBPASE)

[75] Inventors: Adnan M. M. Mjalli, Louisville, Ky.; James Christopher Mason; Kristen Lee Arienti, both of San Diego, Calif.; Kevin Michael Short, Vista, Calif.; Rachel Denise Anne Kimmich, Carlsbad, Calif.; Todd Kevin Jones, Solana Beach, Calif.

[73] Assignee: Ontogen Corporation, Carlsbad, Calif.

[21] Appl. No.: 09/270,121

[22] Filed: Mar. 15, 1999

Related U.S. Application Data

[60] Provisional application No. 60/078,065, Mar. 16, 1998.

[51] Int. Cl.⁷ .............................. A61K 38/12; C07K 5/12
[52] U.S. Cl. .............................. 514/10; 514/11; 514/249; 514/255.02; 530/317; 530/321; 544/344; 544/349; 544/385
[58] Field of Search ................................ 544/344, 349, 544/385; 514/249, 255, 10, 11; 530/317, 321

[56] References Cited

U.S. PATENT DOCUMENTS

| | | | |
|---|---|---|---|
| 4,160,452 | 7/1979 | Theeuwes ................. | 128/260 |
| 4,256,108 | 3/1981 | Theeuwes ................. | 128/260 |
| 4,265,874 | 5/1981 | Bonsen et al. ............. | 424/15 |
| 5,817,751 | 10/1998 | Szardenings et al. .................. | 530/317 |

OTHER PUBLICATIONS

Turner, New therapeutic agents for the treatment of insulin reisitance and NIDDM, *Drug Discovery Today*, 1996, *1*(3):109–116.

Holst, Non–insulin–dependent diabetes mellitus: new drugs?, *Drug Discovery Today*, 1997, 2(4):128–129.

Magnusson et al., Increased Rate of Gluconeoogenesis in type II Diabetes Mellitus a ¹³C Nuclear Magnetic Resonance Study, *J. Clin. Invest.*, 1992, *90*:1323–1327.

Sanchez–Gutierrez et al., Decreased Responsiveness of Basal Gluconeogenesis to Insulin Action in Hepatocytes Isolated from Genetically Obese (fa/fa) Zucker Rats*, *Endocrinology*, *134*(4):1868–1873.

Hers, Mechanisms of Blood Glucose Homeostasis, *J. Inher. Metab. Dis.*, 1990, *13*:395–410.

Benkovic et al., Mechanism of Action of Fructose 1,6–Bisphosphatse, 1980, pp. 46–82.

Vincent et al., Aicariboside Inhibits Gluconeogenesis in Isolated Rat Hepatocytes, 1991, *Purine and Pyrimidine Metabolism in Man VII*, pp. 359–362.

Ugi et al., Multicomponent reactions in organic chemistry, *Endeavor, New Series*, 1994, *18*(3):115–122.

Gordon et al., Reductive alkylation on a solid phase: Synthesis of a Piperazinedione Combinatorial Library, *Bioorganic & Medicinal Chemistry Letters*, 1995, *5*(1):47–50.

Scott et al., Solid Phase Organic Synthesis (SPOS): A novel route to diketopiperazines and diketomorpholines, *Molecular Diversity*, 1995, *1*:125–134.

Szardenings et al., A Simple Procedure for the Solid Phase Synthesis of Diketopiperazine and Diketomorpholine Derivatives, *Tetrahedron*, 1997, *53*(19):6573–6593.

Ugi, Theα–Addition of Immonium Ions and Anions to Isonitriles Accompanied by Secondary Reactions, *Agnew. Chem. Internat.*, 1962, *1*(1):8–20.

Hoffman et al., Chapter 2, Isonitrile Synthesis, *Organic Reactions*, 1971, pp. 9–17.

Widmer, a Convenient Preparation of *t*–Butyl Esters, *Communications*, 1983, pp. 135–136.

Taketa, Allosteric Inhibition of Rat Liver Fructose 1,6–Diphosphatase by Adenosine 5'–Monophosphate*, *The Journal of Biological Chemistry*, 1965, *240*(2):651–662.

*Primary Examiner*—Emily Bernhardt
*Attorney, Agent, or Firm*—Frank S. Chow

[57] ABSTRACT

Compounds of formula A are disclosed:

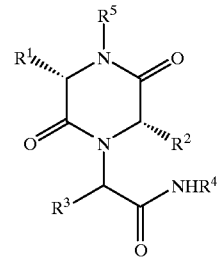

A wherein $R^1$ is aralkyl or cycloalkyl;

$R^2$ is cycloalkylmethyl, alkyl, or aralkyl;

$R^3$ is hydrogen, alkyl, substituted phenyl (including p-phenoxy-phenyl), or fluorene;

$R^4$ is hydrogen, alkyl, substituted phenyls (including 1-alkyl-4-carboxy-substituted phenyls), alkyl carboxylic acids;

$R^5$ is hydrogen or $R^1$ and $R^5$ taken together forming a tetrahydroisoquinoline ring or a piperidine ring.

These compounds exhibit inhibitory action against fructose-1,6-bisphosphatase (FBPase) and are indicated in the treatment or management of Type II diabetes.

21 Claims, No Drawings

PIPERAZINES AS INHIBITORS OF FRUCTOSE-1,6-BISPHOSPHATASE (FBPASE)

This application claims the benefit of the filing date of provisional application serial No. 60/078,065, filed on Mar. 16, 1998, the disclosure of which is incorporated herein by reference.

FIELD OF THE INVENTION

The present invention relates to certain substituted piperazines, which exhibit inhibitory action against fructose-1,6-bisphosphatase (FBPase). These compounds are indicated in the treatment or management of Type-II diabetes.

BACKGROUND

Diabetes is a major international health problem, affecting 100 million people worldwide. In the U.S. alone, 10 million people suffer the effects of diabetes; it is estimated that an additional 5 million people have diabetes, but have not yet been diagnosed. The physical complications that can result from the abnormally high blood glucose levels associated with diabetes are severe. In the U.S., it is the leading cause of end-stage renal failure, lower limb amputation, and blindness in adults over the age of 20. The incidence of heart disease, stroke, and high blood pressure in the diabetic population is more than double that of the non-diabetic population. As a consequence, diabetes is the seventh leading cause of death in the U.S. (Centers for Disease Control and Prevention, National Diabetes Fact Sheet).

Based on pathology and etiology, diabetes is separated into several distinct categories. Type I diabetes, which affects 5–10% of diabetic patients, is characterized by a complete inability of the individual's pancreas to produce insulin as a result of the destruction of pancreatic—islet cells by immune cells. Thus, Type I diabetes is successfully treated only by supplementation with insulin. Type II diabetes, the form that affects ~90% of diabetics, is characterized by resistance to the effects of insulin and an eventual decline in compensatory insulin production. Type II diabetes can be successfully treated with insulin; however insulin therapy in NIDDM often results in weight gain and hypoglycemia. The most common alternatives to insulin therapy for the treatment of Type II diabetes utilize agents that enhance insulin production by pancreatic—islet cells and/or enhance cellular response to insulin (reviewed in Turner, *DDT* 1:109 (1996); Hoist, *DDT* 2:128 (1997)). The currently available therapies have substantial side effects that can limit their usefulness.

Type II diabetic individuals generally exhibit poor control over blood glucose levels, which is manifested as persistent and sustained elevation in glucose levels following food consumption as well as by unusually high blood glucose levels during fasting periods. The acute hyperglycemia experienced after eating is due to diminished glucose uptake from the blood by bodily tissues such as adipose and skeletal muscle, most likely the result of resistance to the normal effects of insulin on these tissues. The relative hyperglycemia experienced by the Type II diabetic patient during periods of fasting is believed to be due to increased glucose production (gluconeogenesis) by cells in the liver (Magnusson, et. al., *J. Clin. Invest.* 90:1323 (1992)), which may also result from decreased hepatic responsiveness to insulin (Sanchez-Gutierrez, *Endocrinology* 134:1868 (1994)). Current therapies are directed at decreasing hyperglycemia by increasing uptake of circulating glucose from the blood. However, they do not effectively alleviate the hyperglycemia experienced during fasting periods which results from elevated hepatic gluconeogenesis.

Gluconeogenesis is regulated physiologically at several metabolic points, with the key rate-limiting step being the conversion of fructose-1,6-bisphosphate to fructose-6-phosphate. This step is controlled by the activity of fructose-1,6-bisphosphatase (FBPase), an enzyme which is unique to the gluconeogenesis pathway (reviewed in Hers, *J. Inher. Metab. Dis.* 13:395 (1990); Benkovic and deMaine, *Adv. Enzymol* 53:45 (1982)). In vivo, FBPase activity is controlled by the cellular levels of its inhibitors, adenosine monophosphate (AMP) and fructose-2,6-bisphosphate (F-2, 6-$P_2$; Hers, supra). FBPase activity has been regulated experimentally in vitro and in isolated liver hepatocytes by the use of a naturally occurring analog of AMP, AICA ribose (Vincent, et. al., *Pur. Pyrim. Metab. in Man* 8:359 (1991). Inhibitors of FBPase could logically be predicted to cause decreased blood glucose levels through the inhibition of gluconeogenesis. Because of its unique and critical role in gluconeogenesis, FBPase forms an attractive target for therapeutic intervention for the treatment of hyperglycemia in diabetes or in other diseases where hyperglycemia is manifested.

DESCRIPTION OF PRIOR ART

Processes, for the preparation of compounds below, are known in the chemical arts. See, for example: Ugi, et. al. *Endeavour,* 18:115 (1994).

Diketopiperazine derivatives have also been described in, for example: Gordon, D. W., Steele, J., *BioMed. Chem. Lett.,* 1995, 5, 47–50; Scott, B. O., Siegmund, A. C., Marlowe, C. K., Pei, Y., Spear, K. L., *Mol. Diversity,* 1995, 1, 125–134; Anna Katrin Szardenings, Timothy S. Burkoth, Henry H. Lu, David W. Tien, and David A. Campbell, *Tetrahedron,* 1997, 53, 19, 6573–6593; and *Methods for Synthesis of Diketopiperazine and Diketomorpholine Derivatives,* by Szardenings, Anna Katrin; Campbell, David; U.S. Pat. No. 5,817,751.

We now describe a new group of compounds which are inhibitors of fructose-1,6-bisphosphatase (FBPase).

DETAILED DESCRIPTION

The present invention relates to compounds having the following structural formula as shown in Formula A:

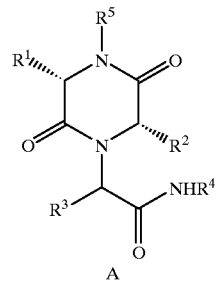

Formula A wherein $R^1$ is aralkyl or cycloalkyl;
$R^2$ is cycloalkylmethyl, alkyl, or aralkyl;
$R^3$ is hydrogen, alkyl, substituted phenyl, or fluorene;
$R^4$ is hydrogen, alkyl, substituted phenyls, or acyl e.g., alkyl carboxylic acids;
$R^5$ is hydrogen or $R^1$ and $R^5$ taken together forming a tetrahydroisoquinoline ring, or a piperidine ring which may be optionally substituted.

As used herein and in the claims, "alkyl" is intended to include both branched- and straight-chained saturated aliphatic hydrocarbon groups having one to six carbon atoms; "cycloalkyl" is intended to mean saturated ring groups having 3 to 8 carbon atoms such as cyclopropyl, cyclobutyl, cyclopentyl, cyclohexyl and cycloheptyl.

The term "aryl" is intended to mean phenyl or naphthyl and the term "substituted phenyl" is intended to mean "aryl" as defined substituted by one to three members independently selected from the group consisting of amino-, mono- or dialkylamino, aminoalkyl, hydroxyalkyl, hydroxy, alkoxy, nitro, cyano, $CF_3$, halo, CHO, COOH and phenoxy.

The tetrahydroisoquinoline ring or the piperidine ring may be substituted by amino-mono-or dialkylamino, aminoalkyl, hydroxyalkyl, hydroxy, alkoxy, nitro, cyano, $CF_3$, halo, CHO and COOH.

The term "aralkyl" is intended to mean a radical in which "aryl" as defined is substituted for hydrogen of "alkyl" as defined e.g. phenethyl.

More particularly, the present invention relates to compounds of the formulas (I–XXIII), as shown in the following Table 1, or pharmaceutically acceptable salts or esters thereof:

TABLE 1

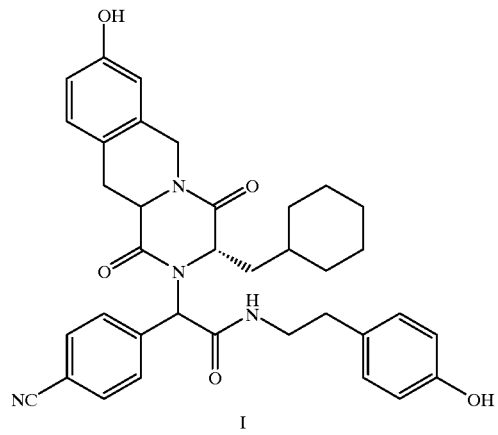

I

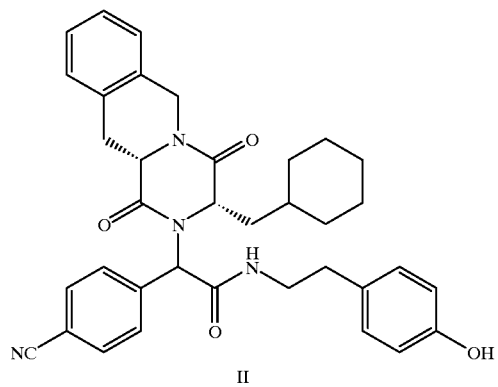

II

TABLE 1-continued

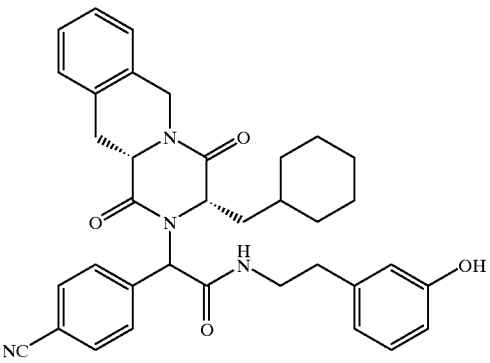

III

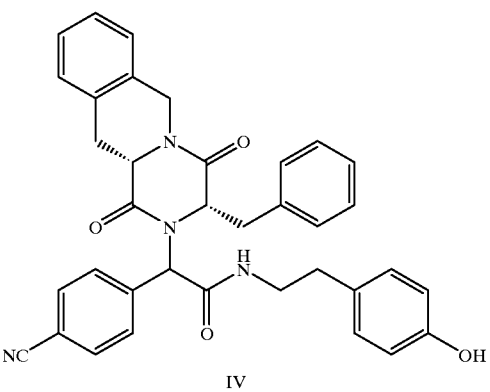

IV

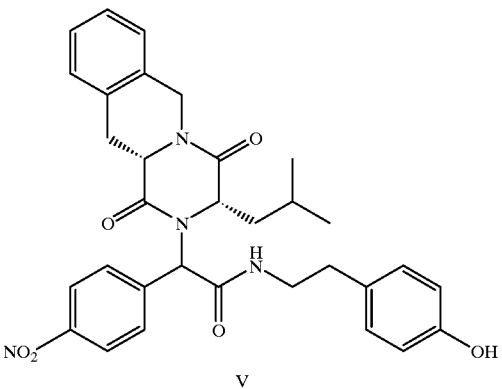

V

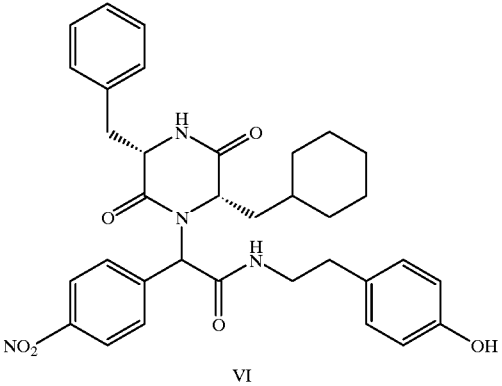

VI

TABLE 1-continued
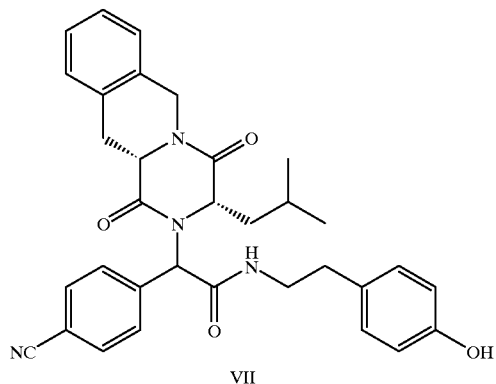
VII
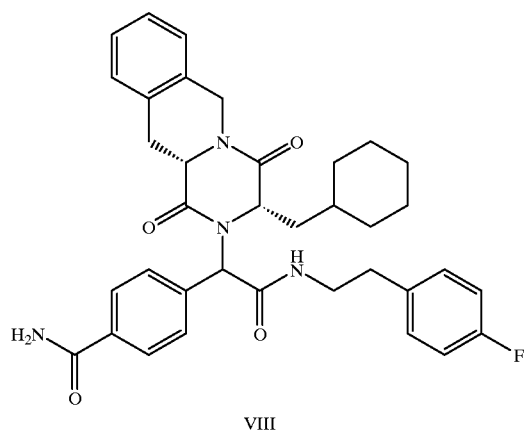
VIII
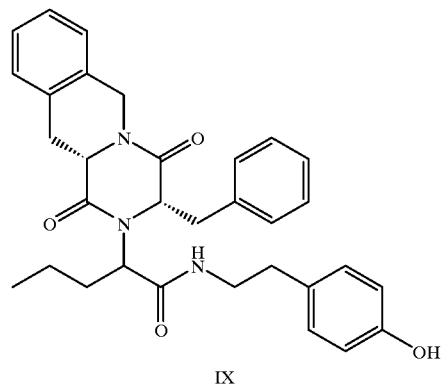
IX
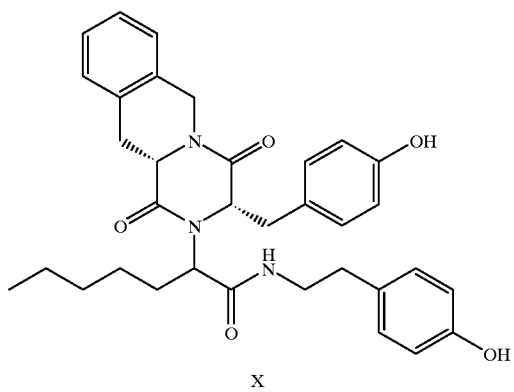
X
TABLE 1-continued
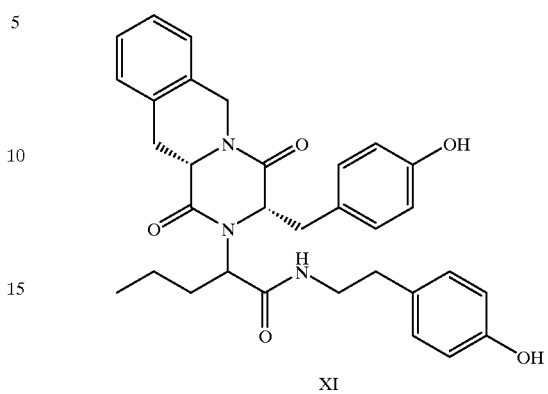
XI
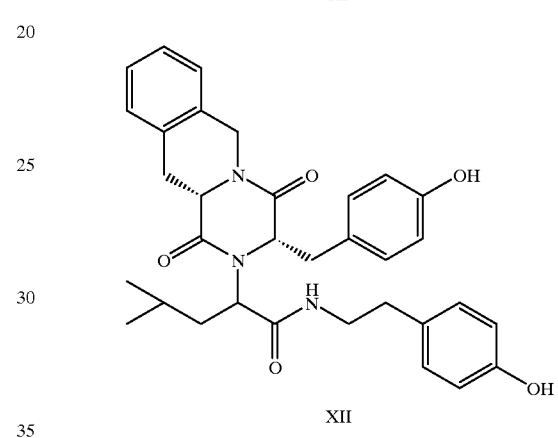
XII
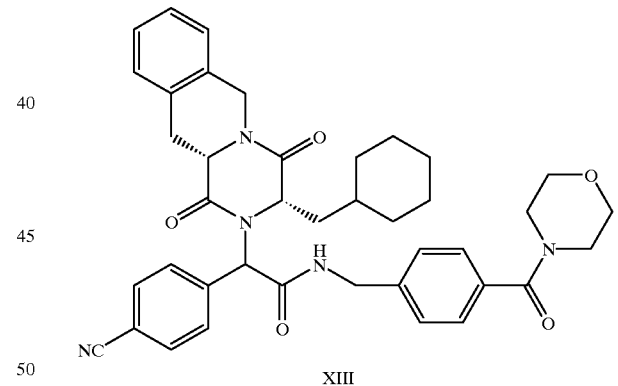
XIII
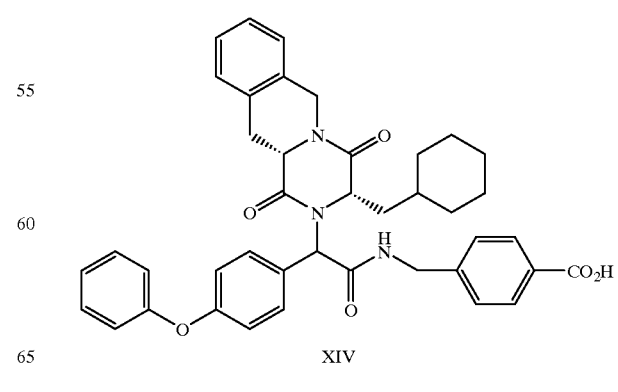
XIV TABLE 1-continued
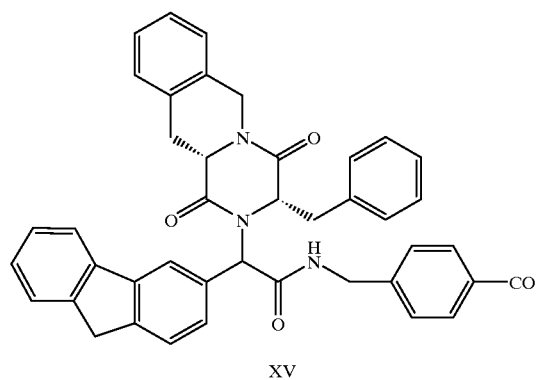
XV
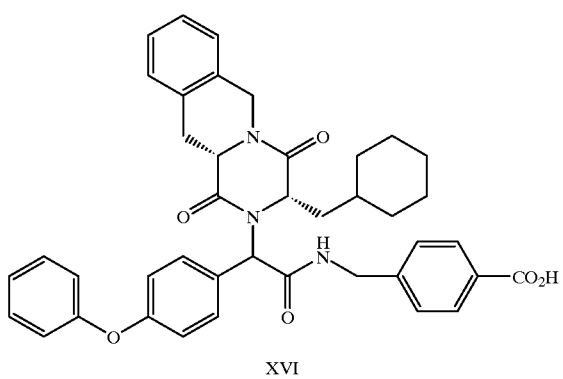
XVI
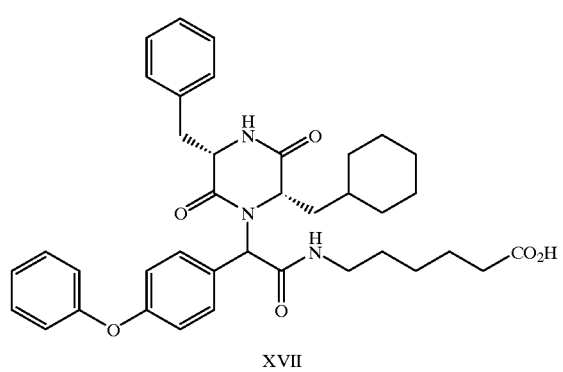
XVII
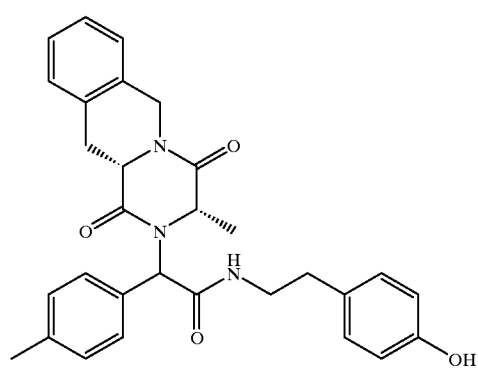
XVIII
TABLE 1-continued
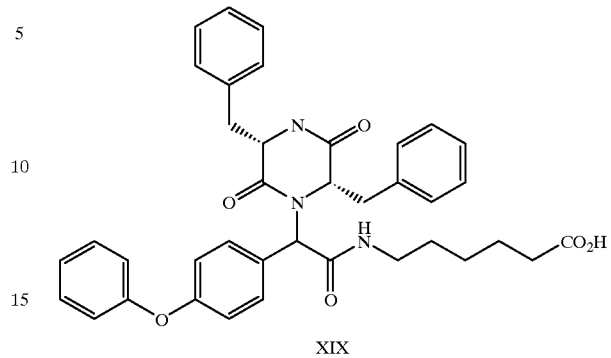
XIX
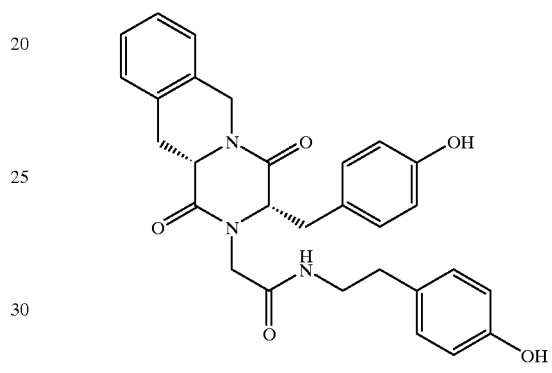
XX
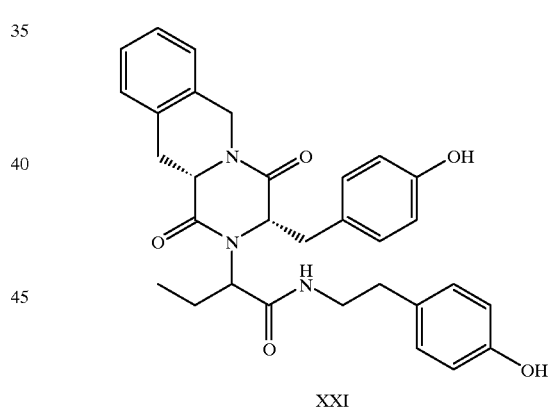
XXI
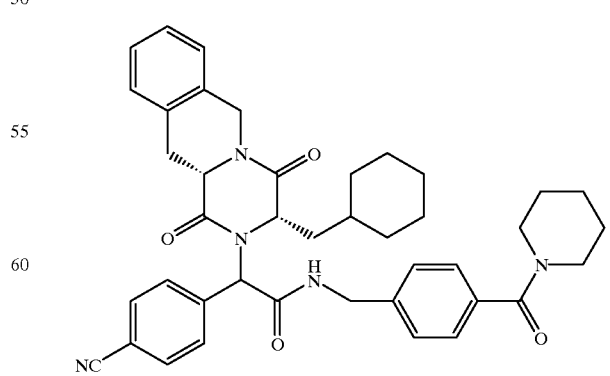
XXII TABLE 1-continued

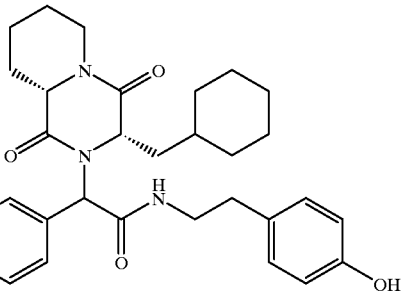

XXIII

The compounds depicted in Table 1 are named as follows:

Compound I 2-(4-Cyano-phenyl)-2-(3-cyclohexylmethyl-8-hydroxy-1,4-dioxo-1,3,4,6,11,11a-hexahydro-pyrazino[1,2-b]isoquinolin-2-yl)-N-[2-(4-hydroxy-phenyl)-ethyl]-acetamide Compound II 2-(4-Cyano-phenyl)-2-(3-cyclohexylmethyl-1,4-dioxo-1,3,4,6,11,11a-hexahydro-pyrazino[1,2-b]isoquinolin-2-yl)-N-[2-(4-hydroxy-phenyl)-ethyl]-acetamide Compound III 2-(4-Cyano-phenyl)-2-(3-cyclohexylmethyl-1,4-dioxo-1,3,4,6,11,11a-hexahydro-pyrazino[1,2-b]isoquinolin-2-yl)-N-[2-(3-hydroxy-phenyl)-ethyl]-acetamide Compound IV 2-(3-Benzyl-1,4-dioxo-1,3,4,6,11,11a-hexahydro-pyrazino[1,2-b]isoquinolin-2-yl)-2-(4-cyano-phenyl)-N-[2-(4-hydroxy-phenyl)-ethyl]-acetamide Compound V N-[2-(4-Hydroxy-phenyl)-ethyl]-2-(3-isobutyl-1,4-dioxo-1,3,4,6,11,11a-hexahydro-pyrazino[1,2-b]isoquinolin-2-yl)-2-(4-nitro-phenyl)-acetamide Compound VI 2-(3-Benzyl-6-cyclohexylmethyl-2,5-dioxo-piperazin-1-yl)-N-[2-(4-hydroxy-phenyl)-ethyl]-2-(4-nitro-phenyl)-acetamide Compound VII 2-(4-Cyano-phenyl)-N-[2-(4-hydroxy-phenyl)-ethyl]-2-(3-isobutyl-1,4-dioxo-1,3,4,6,11,11a-hexahydro-pyrazino[1,2-b]isoquinolin-2-yl)-acetamide Compound VIII 4-{(3-Cyclohexylmethyl-1,4-dioxo-1,3,4,6,11,11a-hexahydro-pyrazino[1,2-b]isoquinolin-2-yl)-[2-(4-fluoro-phenyl)-ethylcarbamoyl]-methyl}-benzamide Compound IX 2-(3-Benzyl-1,4-dioxo-1,3,4,6,11,11a-hexahydro-pyrazino[1,2-b]isoquinolin-2-yl)-pentanoic acid [2-(4-hydroxy-phenyl)-ethyl]-amide Compound X 2-[3-(4-Hydroxy-benzyl)-1,4-dioxo-1,3,4,6,11,11a-hexahydro-pyrazino[1,2-b]isoquinolin-2-yl]-heptanoic acid [2-(4-hydroxy-phenyl)-ethyl]-amide Compound XI 2-[3-(4-Hydroxy-benzyl)-1,4-dioxo-1,3,4,6,11,11a-hexahydro-pyrazino[1,2-b]isoquinolin-2-yl]-pentanoic acid [2-(4-hydroxy-phenyl)-ethyl]-amide Compound XII 2-[3-(4-Hydroxy-benzyl)-1,4-dioxo-1,3,4,6,11,11a-hexahydro-pyrazino[1,2-b]isoquinolin-2-yl]-4-methyl-pentanoic acid [2-(4-hydroxy-phenyl)-ethyl]-amide Compound XIII 2-(4-Cyano-phenyl)-2-(3-cyclohexylmethyl-1,4-dioxo-1,3,4,6,11,11a-hexahydro-pyrazino[1,2-b]isoquinolin-2-yl)-N-[4-(morpholine-4-carbonyl)-benzyl]-acetamide Compound XIV 4-{[2-(3-Cyclohexylmethyl-1,4-dioxo-1,3,4,6,11,11a-hexahydro-pyrazino[1,2-b]isoquinolin-2-yl)-2-(4-phenoxy-phenyl)-acetylamino]-methyl}-benzoic acid Compound XV 4-{[2-(3-Benzyl-1,4-dioxo-1,3,4,6,11,11a-hexahydro-pyrazino[1,2-b]isoquinolin-2-yl)-2-(9H-fluoren-3-yl)-acetylamino]-methyl}-benzoic acid Compound XVI 6-[2-(3-Benzyl-6-cyclohexylmethyl-2,5-dioxo-piperazin-1-yl)-2-(4-phenoxy-phenyl)-acetylamino]-hexanoic acid Compound XVII N-[2-(4-Hydroxy-phenyl)-ethyl]-2-(3-methyl-1,4-dioxo-1,3,4,6,11,11a-hexahydro-pyrazino[1,2-b]isoquinolin-2-yl)-2-p-tolyl-acetamide Compound XVIII 6-[2-[2-Benzyl-5-(4-nitro-benzyl)-3,6-dioxo-piperazin-1-yl]-2-(4-phenoxy-phenyl)-acetylamino]-hexanoic acid Compound XIX 2-[3-(4-Hydroxy-benzyl)-1,4-dioxo-1,3,4,6,11,11a-hexahydro-pyrazino[1,2-b]isoquinolin-2-yl]-N-[2-(4-hydroxy-phenyl)-ethyl]-acetamide Compound XX 2-[3-(4-Hydroxy-benzyl)-1,4-dioxo-1,3,4,6,11,11a-hexahydro-pyrazino[1,2-b]isoquinolin-2-yl]-N-[2-(4-hydroxy-phenyl)-ethyl]-butyramide Compound XXI 2-(4-Cyano-phenyl)-2-(3-cyclohexylmethyl-1,4-dioxo-1,3,4,6,11,11a-hexahydro-pyrazino[1,2-b]isoquinolin-2-yl)-N-[2-(4-methoxy-phenyl)-ethyl]-acetamide Compound XXII 2-(4-Cyano-phenyl)-2-(3-cyclohexylmethyl-1,4-dioxo-1,3,4,6,11,11a-hexahydro-pyrazino[1,2-b]isoquinolin-2-yl)-N-[4-(piperidine-1-carbonyl)-benzyl]-acetamide

Compound XXIII 2-(4-Cyano-phenyl)-2-(3-cyclohexylmethyl-1,4-dioxo-octahydro-pyrido[1,2-a]pyrazin-2-yl)-N-[2-(4-hydroxy-phenyl)-ethyl]-acetamide The compounds of the present invention have asymmetric centers and may occur as racemates, racemic mixtures, and as individual enantiomers or diastereoisomers, with all isomeric forms being included in the present invention as well as mixtures thereof.

Pharmaceutically acceptable salts of the compounds above, where a basic or acidic group is present in the structure, are also included within the scope of this invention. When an acidic substituent is present, such as —$CO_2H$, there can be formed the ammonium, sodium, potassium, calcium salt, and the like, for use as the dosage form. Basic groups, such as amino or basic heteroaryl radicals, or pyridyl and acidic salts, such as hydrochloride, hydrobromide, acetate, maleate, palmoate, methanesulfonate, p-toluenesulfonate, and the like, can be used as the dosage form.

Also, in the case of the —$CO_2H$ being present, pharmaceutically acceptable esters can be employed, e.g., methyl, tert-butyl, pivaloyloxymethyl, acetoxymethyl, and the like, and those esters known in the art for modifying solubility or hydrolysis characteristics for use as sustained release or prodrug formulations.

In addition, some of the compounds of the instant invention may form solvates with water or common organic solvents. Such solvates are encompassed within the scope of the invention.

The term "therapeutically effective amount" shall mean that amount of drug or pharmaceutical agent that will elicit the biological or medical response of a tissue, system, animal, or human that is being sought by a researcher, veterinarian, medical doctor or other clinician.

Syntheses Description

The above mentioned compounds are synthesized using the Ugi 4-component-condensation (4CC) reaction (Ugi, I. *Angew. Chem. Int. Ed. Engl.* 1962, 1, 8). Methyl esters of—amino acids of general Formula 2 (amine input), isocyanides of general Formula 3, aldehydes of general Formula 4, and 9-fluorenylmethoxycarbonyl(Fmoc)-protected—amino acids of general Formula 5 (acid input) are combined in a one pot reaction to form an—acylamino amide of general Formula B which is allowed to cyclize to the diketopiperazine derivative of general Formula A as shown in Scheme 1.

Most Ugi reactions are carried out in methanol/methylene chloride or methanol/trimethylorthoformate mixtures at room temperature, using zinc chloride for the reaction of aromatic aldehydes and triethylamine upon use of the hydrochloride salt of the amine. Due to the newly-formed stereocenter from the aldehyde, the resulting intermediate of general Formula B is formed as a pair of diastereomers. Cyclization further takes place upon N-deprotection of the amine of general Formula B to afford the diketopiperazine compounds of general Formula A.

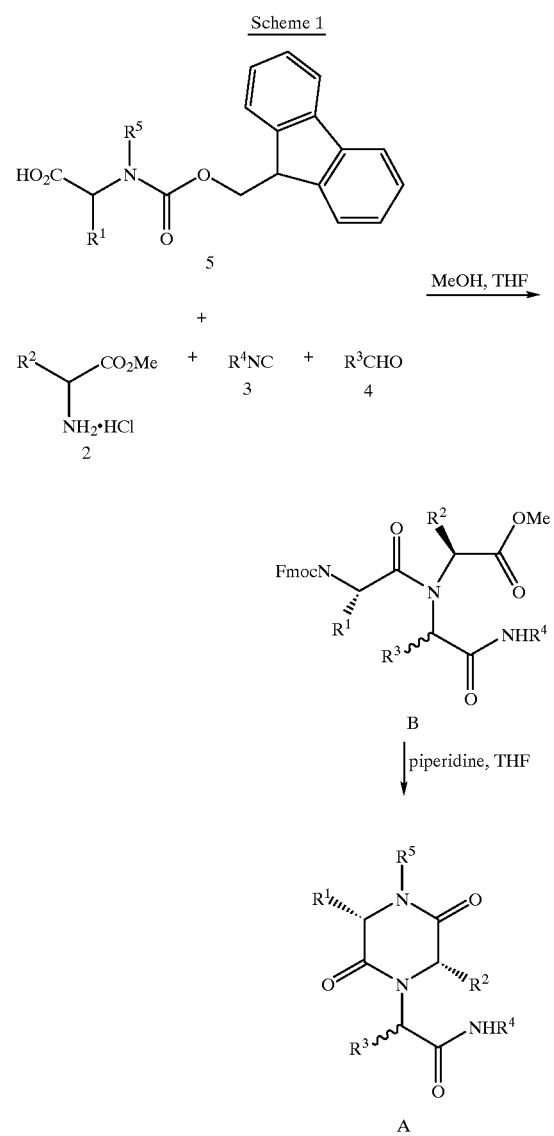

The isocyanides of Formula 3 are either commercially available or synthesized from the corresponding amines 6 via the formamides 7, as shown in Scheme 2.

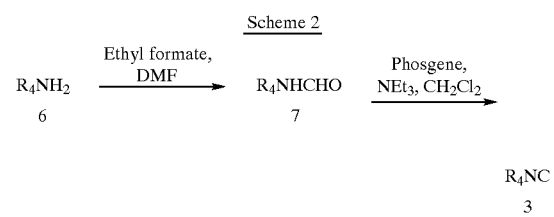

Reaction of the amines of general Formula 6 with ethyl formate in dimethylformamide can be refluxed at 100° C. and generally affords the clean N-formyl compounds of general Formula 7. These are then reacted with phosgene and triethylamine in methylenechloride to afford, after a few hours at room temperature, the isocyanide of general Formula 3 (Hoffmann, Ugi, "*Isonitrile Chemistry*", in "Organic Reactions", Academic Press, New York, 1971, 10–17). After extraction with sodium bicarbonate and a rapid flash chromatography on silica gel or possibly triethylamine-deactivated silica gel, these compounds can be stored at −25° C. before use in Ugi 4-component-condensation reactions.

More generally, isocyanides of general Formula 9 are prepared as shown in Scheme 3 by sequential protection of 4-hydroxy-phenyl-ethylamine, 4-carboxy-phenyl-ethylamine, or 4-carboxy-benzylamine, via either benzyl-ethers or esters, or tert-butyl esters (U. Widmer, *Communications,* 1983, 135–136), followed by formylation. The resulting formylated amines are further dehydrated as described above to afford isocyanides of general Formula 9.

The compounds of general Formula A described herein are also synthesized on solid-phase support as shown in Scheme 4. A preformed resin-supported isocyanide of general Formula 10 is combined in sequential fashion with aldehydes of general Formula 4, Fmoc-N-protected—amino acids of general Formula 5 and methyl-ester-protected—amino acids of general Formula 2 to form the solid-phase-bound—acylamino amide of general Formula 11 which is allowed to cyclize to form the solid-phase-bound diketopiperazine compound of general Formula 12 by cleavage of the Fmoc-N-protecting group of the amine input. The diketopiperazine is further cleaved from the resin support with a trifluoroacetic acid/methylene chloride mixture to give the compound of general Formula A.

The Ugi 4CC reaction on solid support (Wang resin) is generally carried out over a few days in a tetrahydrofuran/methanol mixture with or without zinc chloride and triethylamine, accordingly. The resin-bound compound is further washed several times with solvents such as acetone, methanol, water, and/or methylene chloride. The resin-bound compound is then treated with 20% piperidine in methylene chloride and washed again according to general solid-phase chemistry procedures. The resulting compound of general Formula A cleaved off the solid support is further purified according to general solution-phase-chemistry procedures.

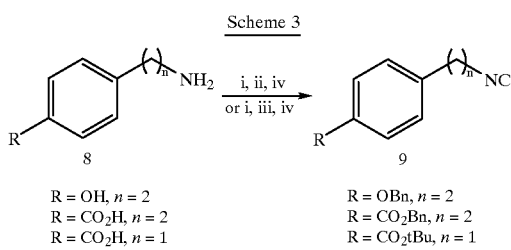

Scheme 3

R = OH, n = 2     R = OBn, n = 2
R = CO₂H, n = 2   R = CO₂Bn, n = 2
R = CO₂H, n = 1   R = CO₂tBu, n = 1 i: ethyl formate, DMF, 100° C.; ii: BnBr, K₂CO₃, DMF,
iii: N, N-dimethylformamide di-tert-butyl acetal, toluene, 80° C.; iv: phosgene, NEt₃, CH₂Cl₂

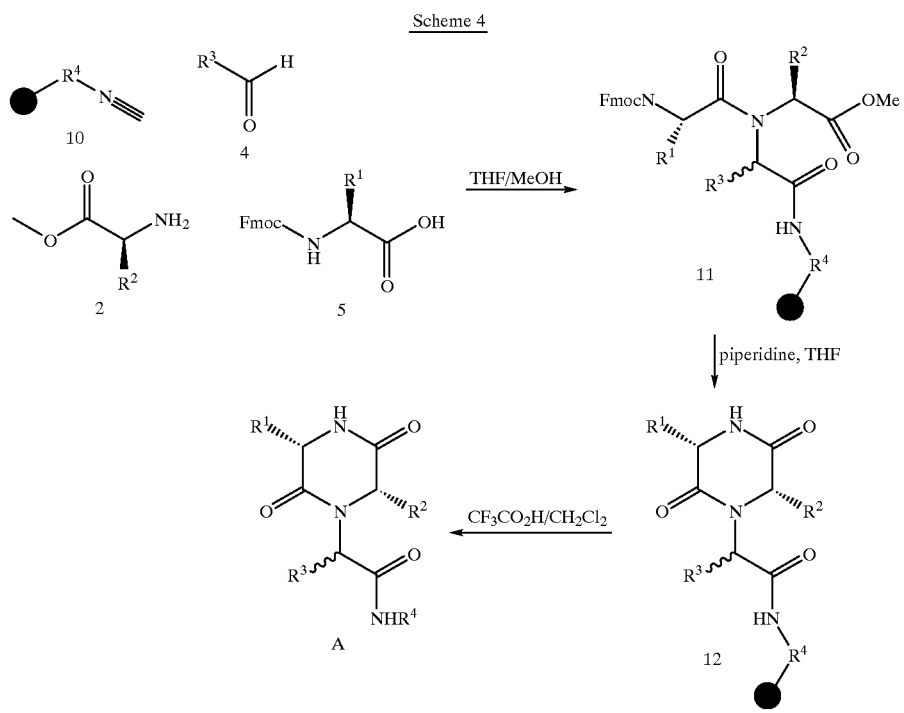

Scheme 4

Biological Assay

The above compounds are assayed utilizing the procedure described by Taketa and Pogell (*J. Biol. Chem.* 240:651 (1965)), wherein the conversion of fructose-1,6-bisphosphate to fructose-6-phosphate is measured by monitoring the conversion of NADP to NADPH through two coupled reactions mediated by phosphoglucose isomerase and glucose-6-phosphate dehydrogenase. The increase in NADPH concentration during the course of the reactions was determined by measuring the increase in absorption at 340 nm. The controls used in the assay were adenosine monophosphate CAMP, $1(_{50}\ 1.4\pm0.5\ \mu M)$ and fructose 2.6-bisphosphate $(1(_{50}\ 2.9\pm0.9\ \mu M)$. The results obtained of the above compounds are as follows (Table 2):

TABLE 2

|      | $IC_{50}$ ($\mu M$) |
|------|------|
| I    | 0.37 |
| II   | 2.1  |
| III  | 8    |
| IV   | 15   |
| V    | 21   |
| VI   | 24   |
| VII  | 30   |
| VIII | 32   |
| IX   | 34   |
| X    | 40   |
| XI   | 45   |
| XII  | 54   |
| XIII | 57   |
| XIV  | 24   |
| XV   | 27   |
| XVI  | 34   |
| XVII | 37   |
| XVIII| 95   |

In Table 2, $IC_{50}$ represents the concentration of inhibitor, which would result in 50% inhibition of FBPase activity. The Roman numbers designate the compounds' numbers as depicted in Formula A for which inhibition of FBPase activity has been measured.

The compounds above exhibit inhibitory activity against fructose-1,6-bisphosphatase (FIBPase). As discussed above, inhibition of this enzyme would logically result in the lowering of blood sugar. These compounds are indicated in the treatment or management of Type-II diabetes.

The present invention also has the objective of providing suitable topical, oral, and parenteral pharmaceutical formulations for use in the novel methods of treatment of the present invention. The compounds of the present invention may be administered orally as tablets, aqueous or oily suspensions, lozenges, troches, powders, granules, emulsions, capsules, syrups or elixirs. The composition for oral use may contain one or more agents selected from the group of sweetening agents, flavoring agents, coloring agents and preserving agents in order to produce pharmaceutically elegant and palatable preparations. The tablets contain the acting ingredient in admixture with non-toxic pharmaceutically acceptable excipients which are suitable for the manufacture of tablets. These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,452; and 4,265,874 to form osmotic therapeutic tablets for control release.

Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such excipients may be (1) suspending agent such as sodium carboxymethyl cellulose, methyl cellulose, hydroxypropylmethylcellulose, sodium alginate, polyvinylpyrrolidone, gum tragacanth and gum acacia; (2) dispersing or wetting agents which may be (a) a naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be formulated as a suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The compounds may also be administered in the form of suppositories for rectal administration of the drug. These compositions can be prepared by mixing the drug with a suitable non-irritating excipient which is solid at ordinary temperature but liquid at the rectal temperature and will therefore melt in the rectum to release the drug. Such materials include cocoa butter and polyethylene glycols.

The compounds of the present invention may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

For topical use, creams, ointments, jellies, solutions or suspensions, etc., containing the above compounds are employed.

Dosage levels of the compounds of the present invention are of the order of about 0.5 mg to about 100 mg per kilogram body weight, with a preferred dosage range between about 20 mg to about 50 mg per kilogram body weight per day (from about 25 mg to about 5 gms per patient per day). The amount of active ingredient that may be combined with the carrier materials to produce a single dosage will vary depending upon the host treated and the particular mode of administration. For example, a formulation intended for oral administration to humans may contain 5 mg to 1 g of an active compound with an appropriate and convenient amount of carrier material which may vary from about 5 to about 95 percent of the total composition. Dosage unit forms will generally contain between from about 5 mg to about 500 mg of active ingredient.

To enhance the therapeutic activity of the present compounds they may be administered concomitantly with others orally active antidiabetic compounds such as the sulfonylureas, e.g., tolbutamide and the like.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Experimental Synthetic Description

In order to further illustrate the practice of this invention, the following examples are included along with the general methods employed to synthesize the compounds described.

General Experimental Information

Nuclear magnetic resonance spectra ($^1$H-NMR) were measured on either a Varian (300 MHz) or a Varian (400 MHz). Chemical shifts ( ) are reported in parts per million (ppm) downfield from tetramethylsilane (TMS). Data are reported as follows: chemical shift, multiplicity (br.=broad, s=singlet, d=doublet, t=triplet, q=quadruplet, m=multiplet), coupling constant (Hz), integration and peak assignment.

Mass spectra were measured using Atmospheric Pressure Chemical Formation (APcI) looking at positive and negative modes on a Micromass LCZ (3 KeV with a probe temperature of 400° C. and a source block at 120° C.).

LC spectra for LC/MS were measured using an eluant of $CH_3CN$ (0.1% $CF_3CO_2H$)/$H_2O$ (0.1% $CF_3CO_2H$) (V:V) on a Hewlett Packard HP1100 HPLC, in the range 200–300 nm with a Diode Array Detector (DAD); 5 1 per injection (Gilson 215 Autosampler) at an average concentration of 1 mg/ml; gradient: 10–100% $CH_3CN$ in 5 minutes, 100% $CH_3CN$ for 1 minute, 100– 10% $CH_3CN$ in 0.2 minutes, 10% $CH_3CN$ for 1.4 minutes; LC element split 1:4 directly into ion source (500 l/min).

The chromatography columns used for LC in LC/MS and HPLC were 50×4.6 mm C-8 with 5 m particle sizes and Zorbax 150×4.6 mm C-8 with 5 m particle sizes, respectively. The same gradient was used in HPLC as in LC for LC/MS.

Reactions in solution phase were monitored by thin layer chromatography (TLC) using Merck silica gel 60F-254-coated plates (0.25 mm thickness). Flash chromatography was performed using E. Merck silica gel 60 (230–400 mesh ASTM).

General Methods
General Method 1: Ugi four-component condensation and piperidine-induced cyclization.

To a flame-dried round bottom flask containing an L-amino acid methyl ester of structure A (1.0 equiv) in $ZnCl_2$ (1.0 equiv, 0.5M in THF) was added triethylamine (1.0 equiv), an aldehyde of structure B (1.0 equiv) and stirred at room temperature for 1 hour under $N_2$. In a separate flask containing an N-fluorenylmethoxycarbonyl (Fmoc)-protected L-amino acid of structure C in $CH_2Cl_2$/MeOH (3:1, 4 mL/mmol) was added an isocyanide of structure D (1.0 equiv). To the isocyanide/amino acid mixture was added the imine and stirred at 50° C. under $N_2$ for 72–96 hours. The solvent was removed under reduced pressure and the diastereomers were purified by flash chromatography as indicated.

To a flame-dried flask containing the synthesized Ugi four-component-condension product in freshly-distilled $CH_2Cl_2$ (10 mL/mmol) was added piperidine (1.0 equiv) and stirred at room temperature for 1 hour under $N_2$. The solvent was removed under reduced pressure and the resulting residue was dissolved in EtOAc and partitioned with water. The aqueous layer was adjusted to pH 4, extracted with EtOAc (3×30 mL) and washed with brine (1×50 mL). The organic solution was dried ($Na_2SO_4$), concentrated under reduced pressure and purified by flash chromatography as indicated. Epimerization of each of the above-described diastereomers was observed in some cases upon piperidine-induced cyclization.

General Method 2: Hydrogenation of a Benzyl Ester or Benzyl Ether.

To a solution of a benzyl ester in 1:1 EtOAc/EtOH (13 mL/mmol) was added 10% Pd-C (10% by weight). The flask was flushed and evacuated with $N_2$ (3×), then stirred under an atmosphere of $H_2$ for 6 hours. The reaction mixture was filtered through Celite, washed with EtOAc (2×20 mL/mmol) then MeOH (2×20 mL/mmol) and concentrated under reduced pressure to give the desired product as an off white solid, which was purified on silica gel as indicated.

General Method 3: Hydrolysis of a T-Butyl Ester.

A solution of a t-butyl ester in 1:1 $CH_2Cl_2$/$CF_3CO_2H$ (10 ml/mmol) was stirred under a $N_2$ atmosphere for 3–4 hours. The reaction mixture was evaporated under high vacuum at room temperature and dried under high vacuum. The residue was dissolved several times in $CH_2Cl_2$, evaporated and dried under high vacuum, in order to eliminate all the remaining $CF_3CO_2H$.

General Method 4: Solid-Phase Ugi Four-Component Condensation, Piperidine-Induced Cyclization, and Acid Cleavage From Resin.

To a round-bottom flask was added resin-supported isocyanide (Z), followed by dry THF (10 ml), MeOH (6 ml). In sequential fashion was added zinc chloride (10 equiv), triethylamine (10 equiv), aldehyde (10 equiv.) and—amino acid, methyl ester hydrochloride (X). The mixture was stirred for 1 hour at room temperature, then to it added Fmoc-—amino acid (Y). This mixture was then stirred for five days, then filtered through a glass frit. The resin was washed with acetone (4×), methanol (4×), water (3×) and finally dichloromethane (6×). The resin was then agitated with a solution of piperidine in THF (1:4) for 40 minutes, then filtered again. The resin was washed with methanol (4×) and dichloromethane (5×). Finally, the resin was agitated with a solution of trifluoroacetic acid in dichloromethane (1:4) for 40 minutes. The resin was filtered, washed with dichloromethane (2×), then the filtrate evaporated to an oil. Flash column chromatography yielded the required product.

EXAMPLE 1

2-(4-Cyano-phenyl)-2-(3-cyclohexylmethyl-8-hydroxy-1,4-dioxo-1,3,4,6,11,11a-hexahydro-pyrazino[1,2-b]isoquinolin-2-yl)-N-[2-(4-hydroxyphenyl)-ethyl]-acetamide (Compound I of Table 1, structure of Formula A, where $R^1$, $R^5$=fused 7-hydroxy tetrahydroisoquinoline, $R^2$=cyclohexylmethyl, $R^3$=4-cyanophenyl, $R^4$=(4-hydroxyphenyl)-ethyl)

phenol benzyl ether (86 mg, 0.36 mmol), triethylamine (50 L, 0.8 mmol), ZnCl$_2$ (1.0 mL, 0.36 mol) and purified by flash chromatography (hex/EtOAc, 3:2) to afford 89 mg (26%) of diastereomer A and 97 mg (28%) of diastereomer B.

Data for diastereomer A: R$_f$ 0.16 (hex/EtOAc, 3:2). Data for diastereomer B: R$_f$ 0.08 (hex/EtOAc, 3:2)

The corresponding cyclized product was prepared from diastereomer B (97 mg, 0.01 mmol), piperidine (10 mL, 0.01 mmol) and purified by flash chromatography (hex/EtOAc, 4:1) to afford 22 mg (31%) of N-[2-(4-benzyloxy-phenyl)-ethyl]-2-(4-cyano-phenyl)-2-(3-cyclohexylmethyl-8-hydroxy-1,4-dioxo-1,3,4,6,11,11a-hexahydro-pyrazino[1,2-b]isoquinolin-2-yl)-acetamide (diastereomer B).

Data for N-[2-(4-benzyloxy-phenyl)-ethyl]-2-(4-cyano-phenyl)-2-(3-cyclohexylmethyl-8-hydroxy-1,4-dioxo-1,3,4,6,11,11a-hexahydro-pyrazino[1,2-b]isoquinolin-2-yl)-acetamide: R$_f$ 0.31 (CH$_2$Cl$_2$/MeOH, 20:1), LC/MS: LC: retention time 3.98 minutes; 697.9 (100%, [M+H]$^+$).

2-(4-Cyano-phenyl)-2-(3-cyclohexylmethyl-8-hydroxy-1,4-dioxo-1,3,4,6,11,11a-hexahydro-pyrazino[1,2-b]isoquinolin-2-yl)-N-[2-(4-hydroxyphenyl)-ethyl]-acetamide (Compound I of Table 1, structure of Formula A, where R$^1$, R$^5$=fused 7-hydroxy tetrahydroisoquinoline, R$^2$=cyclohexylmethyl, R$^3$=4-cyanophenyl, R$^4$=(4-hydroxyphenyl)-ethyl).

This compound was prepared by General Method 2 from N-[2-(4-benzyloxy-phenyl)-ethyl]-2-(4-cyano-phenyl)-2-(3-cyclohexylmethyl-8-hydroxy-1,4-dioxo-1,3,4,6,11,11a-hexahydro-pyrazino[1,2-b]isoquinolin-2-yl)-acetamide (diastereomer B) (10.0 mg, 0.01 mmol) and purified by flash chromatography (hex/EtOAc, 4:1) to afford 6.1 mg (71%) of Compound I. Data for Compound I: R$_f$ 0.17 (CH$_2$Cl$_2$/MeOH, 20:1). $^1$H-NMR (300 MHz, acetone-d$_6$): 8.33 (s, 1H), 8.17 (s, 1H), 7.80 (d, 2H, J=8.2), 7.65 (d, 2H, J=8.2), 7.48 (t, 1H, J=5.7), 7.07–7.00 (m, 3H), 6.75–6.68 (m, 3H), 5.67 (s, 1H), 5.24 (d, 1H, J=17.3), 4.32 (dd, 2H, J=12.5, 4.0), 4.08 (d, 1H, J=17.0), 3.55–3.40 (m, 3H), 3.15 (dd, 1H, J=15.9, 4.1), 2.95–2.81 (m, 1H), 2.71 (t, 2H, J=7.1), 1.61–1.02 (br m, 10H), 0.78–0.62 (m, 1H), 0.46–0.38 (m, 1H).

EXAMPLE 2

2-(4-Cyano-phenyl)-2-(3-cyclohexylmethyl-1,4-dioxo-1,3,4,6,11,11a-hexahydro-pyrazino[1,2-b]isoquinolin-2-yl)-N-[2-(4-hydroxy-phenyl)-ethyl]-acetamide (Compound II of Table 1, structure A of Formula A, where R$^1$, R$^5$=fused tetrahydroisoquinoline, R$^2$=cyclohexylmethyl, R$^3$=4-cyanophenyl, R$^4$=4-hydroxyphenyl ethyl)

N-[2-(4-Benzyloxy-phenyl)-ethyl]-2-(4-cyano-phenyl)-2-(3-cyclohexylmethyl-1,4-dioxo-1,3,4,6,11,11a-hexahydro-pyrazino[1,2-b]isoquinolin-2-yl)-acetamide (structure of Formula A, where R$^1$, R$^5$=fused tetrahydroisoquinoline, R$^2$=cyclohexylmethyl, R$^3$=4-cyanophenyl, R$^4$=4-benzyloxy-phenyl ethyl)

This compound was prepared by General Method 1 from cyclohexyl-L-alanine methyl ester hydrochloride (988 mg, 5.8 mmol), 4-cyanobenzaldehyde (769 mg, 5.9 mmol), Fmoc-1,2,3,4-tetrahydroisoquinoline-3-carboxylic acid (2.4 g, 6.1 mmol), triethylamine (0.83 ml, 6.0 mmol), 12 ml of 0.5 M zinc chloride in tetrahydrofuran and 4-(2-isocyano-ethyl)-phenol benzyl ether (1.42 g, 6.1 mmol), and purified by flash chromatography (1:3 EtOAc/hex) to afford 1.4 g (1.5 mmol) of diastereomer A. Data for diastereomer A: MS(APcI): 936 (5, [M]$^+$), 709 (100), 608 (50), 579 (75); exact mass calcd for C$_{59}$H$_{59}$N$_4$O$_7$ ([M]$^+$) 936.

The uncyclized product diastereomer A (1.0 g, 1.06 mmol) was dissolved in 8 ml of dichloromethane and 2.0 ml of piperidine. After 1 hour the solvent was removed and the residue placed under vacuum. The crude product was purified by flash chromatography to give 428 mg (62%) of N-[2-(4-benzyloxy-phenyl)-ethyl]-2-(4-cyano-phenyl)-2-(3-cyclohexylmethyl-1,4-dioxo-1,3,4,6,11,11a-hexahydro-pyrazino[1,2-b]isoquinolin-2-yl)-acetamide (diastereomer A) and 30 mg (4%) of N-[2-(4-benzyloxy-phenyl)-ethyl]-2-(4-cyano-phenyl)-2-(3-cyclohexylmethyl-1,4-dioxo-1,3,4,6,11,11a-hexahydro-pyrazino[1,2-b]isoquinolin-2-yl)-acetamide (diastereomer B).

Data for N-[2-(4-benzyloxy-phenyl)-ethyl]-2-(4-cyano-phenyl)-2-(3-cyclohexylmethyl-1,4-dioxo-1,3,4,6,11,11a-hexahydro-pyrazino[1,2-b]isoquinolin-2-yl)-acetamide (diastereomer A): R$_f$=0.43 (1:1, EtOAc/hex); $^1$H-NMR (400 MHz, CDCl$_3$): 7.65 (d, 2H, J=8.6), 7.4–6.9 (m, 11H), 7.03 (d, 2H, J=8.6), 6.87 (d, 2H, J=8.7), 6.36 (t, 1H, J=5.6), 5.40 (d, 1H, J=17.2), 5.02 (s, 2H), 4.89 (s, 1H), 4.22 (dd, 1H, J=12.4, 3.8), 4.13 (d, 1H, J=17.4), 4.06 (dd, 1H, J=9.3, 5.8), 3.54 (m, 2H), 3.26 (dd, 1H, J=16.1, 3.8), 2.95 (t, 1H, J=12.8), 2.76 (t, 2H, J=6.8), 1.7–1.4 (m, 9H), 1.07 (m, 4H), 0.83 (q, 1H, J=12.3), 0.65 (q, 1H, J=12.3).

Data for N-[2-(4-Benzyloxy-phenyl)-ethyl]-2-(4-cyano-phenyl)-2-(3-cyclohexylmethyl-1,4-dioxo-1,3,4,6,11,11a-hexahydro-pyrazino[1,2-b]isoquinolin-2-yl)-acetamide (diastereomer B): R$_f$=0.12 (1:1, EtOAc/hex). $^1$H-NMR (400 MHz, CDCl$_3$): 7.65 (d, 2H, J=8.6), 7.4–6.9 (m, 11H), 7.03 (d, 2H, J=8.6), 6.87 (d, 2H, J=8.7), 6.02 (t, 1H, J=5.6), 5.40 (d, 1H, J=17.2), 5.25 (s, 1H), 5.02 (s, 2H), 4.22 (dd, 1H, J=12.4, 3.8), 4.13 (d, 1H, J=17.4), 4.06 (dd, 1H, J=9.3, 5.8), 3.54 (m, 2H), 3.26 (dd, 1H, J=16.1, 3.8), 2.95 (t, 1H, J=12.8), 2.76 (t, 2H, J=6.8), 1.7–1.4 (m, 9H), 1.07 (m, 4H), 0.83 (q, 1H, J=12.3), 0.65 (q, 1H, J=12.3)

2-(4-Cyano-phenyl)-2-(3-cyclohexylmethyl-1,4-dioxo-1,3,4,6,11,11a-hexahydro-pyrazino[1,2-b]isoquinolin-2-yl)-N-[2-(4-hydroxy-phenyl)-ethyl]-acetamide (Compound II of Table 1, structure of Formula A, where R$^1$, R$^5$=fused tetrahydroisoquinoline, R$^2$=cyclohexylmethyl, R$^3$=4-cyanophenyl, R$^4$=4-hydroxyphenyl ethyl)

This compound was prepared by General Method 2 from N-[2-(4-benzyloxy-phenyl)-ethyl]-2-(4-cyano-phenyl)-2-(3-cyclohexylmethyl-1,4-dioxo-1,3,4,6,11,11a-hexahydro-pyrazino[1,2-b]isoquinolin-2-yl)-acetamide (diastereomer A) (100 mg, 0.15 mmol) to afford 55 mg (63%) of 2-(4-cyano-phenyl)-2-(3-cyclohexylmethyl-1,4-dioxo-1,3,4,6,11,11a-hexahydro-pyrazino[1,2-b]isoquinolin-2-yl)-N-[2-(4-hydroxy-phenyl)-ethyl]-acetamide.

Data for 2-(4-Cyano-phenyl)-2-(3-cyclohexylmethyl-1,4-dioxo-1,3,4,6,11,11a-hexahydro-pyrazino[1,2-b]isoquinolin-2-yl)-N-[2-(4-hydroxy-phenyl)-ethyl]-acetamide: R$_f$=0.85 (1:4 acetone/dichloromethane). $^1$H-NMR (400 MHz, CDCl$_3$): 7.65 (d, 2H, J=8.6), 7.4–6.9 (m, 6H), 7.03 (d, 2H, J=8.6), 6.87 (d, 2H, J=8.7), 6.36 (t, 1H, J=5.6), 5.40 (d, 1H, J=17.2), 4.89 (s, 1H), 4.22 (dd, 1H, J=12.4, 3.8), 4.13 (d, 1H, J=17.4), 4.06 (dd, 1H, J=9.3, 5.8), 3.54 (m, 2H), 3.26 (dd, 1H, J=16.1, 3.8), 2.95 (t, 1H, J=12.8), 2.76 (t, 2H, J=6.8), 1.7–1.4 (m, 9H), 1.07 (m, 4H), 0.83 (q, 1H, J=12.3), 0.65 (q, 1H, J=12.3)

EXAMPLE 3

2-(4-Cyano-phenyl)-2-(3-cyclohexylmethyl-1,4-dioxo-1,3,4,6,11,11a-hexahydro-pyrazino[1,2-b]isoquinolin-2-yl)-N-[2-(3-hydroxy-phenyl)-ethyl]-acetamide (Compound III of Table 1, structure of Formula A, where R$^1$, R$^5$=fused tetrahydroisoquinoline, R$^2$cyclohexylmethyl, R$^3$=cyanophenyl, R$^4$=(3-hydroxyphenyl)-ethyl).

N-[2-(3 -Benzyloxy-phenyl)-ethyl]-2-(4-cyano-phenyl)-2-(3-cyclohexylmethyl-1,4-dioxo-1,3,4,6,11,11a- hexahydro-pyrazino[1,2-b]isoquinolin-2-yl)-acetamide (structure of Formula A, where $R^1$, $R^5$=fused tetrahydroisoquinoline, $R^2$=cyclohexylmethyl, $R^3$=cyanophenyl, $R^4$=(3-benzyloxy-phenyl)-ethyl).

This compound was prepared by General Method 1 from cyclohexyl-L-alanine methyl ester hydrochloride (185 mg, 0.80 mmol), 4-cyanobenzaldehyde (110 mg, 0.80 mmol), Fmoc-1,2,3,4-tetrahydroisoquinoline-3-carboxylic acid (330 mg, 0.80 mmol), 4-(2-isocyano-ethyl)-phenol benzyl ether (200 mg, 0.80 mmol), triethylamine (85 mg, 0.8 mmol), $ZnCl_2$ (1.6 mL, 0.8 mmol) and purified by flash chromatography (hex/EtOAc, 3:2) to afford 195 mg (25%) of diastereomer A and 163 mg (21%) of diastereomer B.

Data for diastereomer A: $R_f$ 0.55 (hex/EtOAc, 3:2). Data for diastereomer B: $R_f$ 0.38 (hex/EtOAc, 3:2)

The corresponding cyclized product was prepared for each diastereomer (50 mg, 0.05 mmol) with piperidine (5.3 mL, 0.05 mmol) and purified by flash chromatography (hex/EtOAc, 4:1) to afford 12 mg (33%) of N-[2-(3-benzyloxy-phenyl)-ethyl]-2-(4-cyano-phenyl)-2-(3-cyclohexylmethyl-1,4-dioxo-1,3,4,6,11,11a-hexahydro-pyrazino[1,2-b]isoquinolin-2-yl)-acetamide (diastereomer A) and 12 mg (33%) of N-[2-(3-benzyloxy-phenyl)-ethyl]-2-(4-cyano-phenyl)-2-(3-cyclohexylmethyl-1,4-dioxo-1,3,4,6,11,11a-hexahydro-pyrazino[1,2-b]isoquinolin-2-yl)-acetamide (diastereomer B).

Data for N-[2-(3-benzyloxy-phenyl)-ethyl]-2-(4-cyano-phenyl)-2-(3-cyclohexylmethyl-1,4-dioxo-1,3,4,6,11,11a-hexahydro-pyrazino[1,2-b]isoquinolin-2-yl)-acetamide (diastereomer A): $R_f$ 0.83 (EtOAc). LC/MS: LC: retention time 4.58 minutes; 681.3 (100%, [M+H]$^+$). Data for N-[2-(3-benzyloxy-phenyl)-ethyl]-2-(4-cyano-phenyl)-2-(3-cyclohexylmethyl-1,4-dioxo-1,3,4,6,11,11a-hexahydro-pyrazino[1,2-b]isoquinolin-2-yl)-acetamide (diastereomer B): $R_f$ 0.33 (EtOAc). LC/MS: LC: retention time 4.51 minutes; 681.3 (100%, [M+H]$^+$).

2-(4-Cyano-phenyl)-2-(3-cyclohexylmethyl-1,4-dioxo-1,3,4,6,11,11a-hexahydro-pyrazino[1,2-b]isoquinolin-2-yl)-N-[2-(3-hydroxy-phenyl)-ethyl]-acetamide (Compound III of Table 1, structure of Formula A, where $R^1$, $R^5$=fused tetrahydroisoquinoline, $R^2$=cyclohexylmethyl, $R^3$=4-cyanophenyl, $R^4$=(3-hydroxyphenyl)-ethyl).

This compound was prepared by General Method 2 from N-[2-(3-benzyloxy-phenyl)-ethyl]-2-(4-cyano-phenyl)-2-(3-cyclohexylmethyl-1,4-dioxo-1,3,4,6,11,11a-hexahydro-pyrazino[1,2-b]isoquinolin-2-yl)-acetamide (diastereomer A) (12 mg, 0.02 mmol) and purified by flash chromatography (hex/EtOAc, 4:1) to afford 8 mg (80%) of 2-(4-cyano-phenyl)-2-(3-cyclohexylmethyl-1,4-dioxo-1,3,4,6,11,11a-hexahydro-pyrazino[1,2-b]isoquinolin-2-yl)-N-[2-(3-hydroxy-phenyl)-ethyl]-acetamide (diastereomer A of Compound III).

Data for 2-(4-cyano-phenyl)-2-(3-cyclohexylmethyl-1,4-dioxo-1,3,4,6,11,11a-hexahydro-pyrazino[1,2-b]isoquinolin-2-yl)-N-[2-(3-hydroxy-phenyl)-ethyl]-acetamide (diastereomer A): $R_f$ 0.66 (hex/EtOAc, 4:1). $^1$H-NMR (300 MHz, acetone-d$_6$): 8.27 (br s, 1H), 7.81 (d, 2H, J=8.2), 7.67 (d, 2H, J=8.5), 7.47 (t, 1H, J=5.7), 7.28–7.20 (m, 3H), 7.11–7.03 (m, 2H), 6.71–6.65 (m, 2H), 5.68 (s, 1H), 5.33 (d, 1H, J=16.7), 4.40 (dd, 1H, J=12.6, 4.1), 4.32 (dd, 1H, J=9.7, 3.4), 4.17 (d, 1H, J=17.0), 3.58–3.39 (m, 3H), 3.27 (dd, 1H, J=16.0, 3.7), 3.08–2.9 (m, 1H), 2.74 (t, 2H, J=7.0), 1.64–0.85 (br m, 13H), 0.72–0.62 (m, 1H), 0.46–0.34 (m, 1H).

2-(4-Cyano-phenyl)-2-(3-cyclohexylmethyl-1,4-dioxo-1,3,4,6,11,11a-hexahydro-pyrazino[1,2-b]isoquinolin-2-yl)-N-[2-(3-hydroxy-phenyl)-ethyl]-acetamide (Compound III of Table 1, structure of Formula A, where $R^1$, $R^5$=fused tetrahydroisoquinoline, $R^2$=cyclohexylmethyl, $R^3$=4-cyanophenyl, $R^4$=3-hydroxy-pheny).

This compound was prepared by General Method 2 from N-[2-(3-benzyloxy-phenyl)-ethyl]-2-(4-cyano-phenyl)-2-(3-cyclohexylmethyl-1,4-dioxo-1,3,4,6,11,11a-hexahydro-pyrazino[1,2-b]isoquinolin-2-yl)-acetamide (diastereomer B) (12 mg, 0.02 mmol) and purified by flash chromatography (hex/EtOAc, 4:1) to afford 7.5 mg (75%) of Compound III (diastereomer B).

Data for Compound III (diastereomer B): $R_f$ 0.17 (hex/EtOAc, 4:1). $^1$H-NMR (300 MHz, acetone-d$_6$): 8.23 (s, 1H), 7.81 (d, 2H, J=8.5), 7.71 (d, 2H, J=8.5), 7.38 (t, 1H, J=5.9), 7.23–7.19 (m, 3H), 7.08 (t, 1H, J=7.7), 6.71–6.65 (m, 2H), 5.49 (s, 1H), 5.32 (d, 1H, J=16.7), 4.40 (dd, 1H, J=12.4, 4.1), 4.18–4.13 (m, 2H), 3.49–3.42 (m, 2H), 3.35 (dd, 1H, J=16.3, 3.7), 3.13–3.04 (m, 1H), 2.72 (t, 2H, J=7.14), 1.88–1.79 (m, 2H), 1.57–0.86 (br m, 12H), 0.84–0.60 (m, 1H).

EXAMPLE 4

2-(3-Benzyl-1,4-dioxo-1,3,4,6,11,11a-hexahydropyrazino[1,2-b]isoquinolin-2-yl)-2-(4-cyanophenyl)-N-[2-(4-hydroxyphenyl)ethyl]acetamide (Compound IV of Table 1, structure of Formula A, where $R^1$, $R^5$=fused tetrahydroisoquinoline, $R^2$=phenylmethyl, $R^3$=4-cyano-phenyl, $R^4$=4-hydroxy-phenyl-ethyl)

This compound was prepared at room temperature by General Method 4 from L-phenylalanine methyl ester HCl salt (701 mg, 3.3 mmol), p-cyanobenzaldehyde (218 mg, 1.1 mmol), Fmoc-L-TIC (444 mg, 1.1 mmol), 4-(2-isocyanoethyl)phenol, Wang resin ether (241 mg, 1.1 mmol), triethylamine (160 l, 1.1 mmol), $ZnCl_2$ (2.4 ml, 1.1 mmol) and purified by flash chromatography on $SiO_2$ with a gradient of benzene/acetone (15:1–5:1) to afford 0.5 g (46%) of a mixture of diastereomers. $R_f$ 0.38 (2:8 acetone/benzene, eluted twice).

EXAMPLE 5

N-[2-(4-Hydroxyphenyl)ethyl]-2-(3-isobutyl-1,4-dioxo-1,3,4,6,11,11a-hexahydropyrazino[1,2-b]isoquinolin-2-yl)-2-(4-nitro-phenyl)acetamide (Compound V of Table 1, structure of Formula A, where $R^1$, $R^5$=fused tetrahydroisoquinoline, $R^2$=isobutyl, $R^3$=4-nitro-phenyl, $R^4$=4-hydroxy-phenyl-ethyl)

This compound was prepared at room temperature by General Method 4 from L-leucine methyl ester HCl salt (476 mg, 3.3 mmol), p-nitrobenzaldehyde (506 mg, 3.4 mmol), Fmoc-L-TIC (1.30 g, 3.3 mmol), 4-(2-isocyanoethyl) phenol, Wang resin ether (466 mg, 0.3 mmol), triethylamine (465 l, 3.3 mmol), $ZnCl_2$ (436 mg, 3.2 mmol) and purified by flash chromatography on $SiO_2$ with a gradient of benzene/acetone (15:1–5:1) to afford 42 mg of two diastereomers. $R_f$ 0.58, 0.51 (3:7 acetone/benzene). FIA-MS, -ve mode; 615 (M+HCO$_2$H–H$^-$)$^-$, 682.9 (M+CF$_3$CO$_2$H–H$^-$)$^-$.

EXAMPLE 6

2-(3-Benzyl-6-cyclohexylmethyl-2,5-dioxo-piperazin-1-yl)-N-[2-(4-hydroxyphenyl)ethyl]-2-(4-nitrophenyl) acetamide (Compound VI of Table 1, structure of Formula A, where $R^1$=phenylmethyl, $R^5$=H, $R^2$=cyclohexylmethyl, $R^3$=4-nitro-phenyl, $R^4$=4-hydroxy-phenyl-ethyl)

This compound was prepared at room temperature by General Method 1 from L-cyclohexylalanine methyl ester HCl salt (415 mg, 2.2 mmol), p-nitrobenzaldehyde (338 mg, 2.2 mmol), Fmoc-L-Phe (0.87 g, 2.2 mmol), 4-(2-isocyanoethyl)phenol, (300 mg, 2 mmol), triethylamine (312 l, 2.2 mmol), ZnCl$_2$ (305 mg, 2.2 mmol) and purified by flash chromatography on SiO$_2$ with a gradient of benzene/acetone (15:1–5:1) to afford 260 mg and 140 mg of two, separated diastereomers. R$_f$ 0.35, 0.30 (2:8 acetone/benzene).

EXAMPLE 7

2-(4-Cyanophenyl)-N-[2-(4-hydroxyphenyl)ethyl]-2-(3-isobutyl-1,4-dioxo-1,3,4,6,11,11a-hexahydropyrazino[1,2-b]isoquinolin-2-yl)-acetamide (Compound VII of Table 1, structure of Formula A, where R$^1$, R$^5$=fused tetrahydroisoquinoline, R$^2$=isobutyl, R$^3$=4-cyano-phenyl, R$^4$=4-hydroxy-phenyl-ethyl)

This compound was prepared at room temperature by General Method 4 from L-leucine methyl ester HCl salt (465 mg, 3.2 mmol), p-cyanobenzaldehyde (405 mg, 3.1 mmol), Fmoc-L-TIC (1.22 g, 3.1 mmol), 4-(2-isocyanoethyl) phenol, Wang resin ether (437 mg, 0.3 mmol), triethylamine (430 l, 3.1 mmol), ZnCl$_2$ (409 mg, 3.0 mmol) and purified by flash chromatography on SiO$_2$ with a gradient of benzene/acetone (15:1–5:1) to afford 27 mg and 13 mg of two, separated diastereomers. FIA-MS, -ve mode; 595 (M+HCO$_2$H−H$^-$)$^-$, 662.9 (M+CF$_3$CO$_2$H−H$^-$)$^-$.

EXAMPLE 8

4-{(3-Cyclohexylmethyl-1,4-dioxo-1,3,4,6,11,11a-hexahydro-pyrazino[1,2-b]isoquinolin-2-yl)-[2-(4-fluoro-phenyl)-ethylcarbamoyl]-methyl}-benzamide (Compound VIII of Table 1, structure of Formula A, where R$^1$, R$^5$=fused tetrahydroisoquinoline, R$^2$=cyclohexylmethyl, R$^3$=4-carboxamido-phenyl, R$^4$=4-fluorophenyl ethyl)

2-(4-Cyano-phenyl)-2-(3-cyclohexylmethyl-1,4-dioxo-1,3,4,6,11,11a-hexahydro-pyrazino[1,2-b]isoquinolin-2-yl)-N-[2-(4-fluoro-phenyl)-ethyl]-acetamide (structure of Formula A, where R$^1$, R$^5$=fused tetrahydroisoquinoline, R$^2$=cyclohexylmethyl, R$^3$=4-cyano-phenyl, R$^4$=4-fluorophenyl ethyl)

This compound was prepared by General Method 1 from cyclohexyl-L-alanine methyl ester hydrochloride (988 mg, 5.8 mmol), 4-cyanobenzaldehyde (769 mg, 5.9 mmol), Fmoc-1,2,3,4-tetrahydroisoquinoline-3-carboxylic acid (2.4 g, 6.1 mmol), triethylamine (0.83 ml, 6.0 mmol), 12 ml of 0.5 M zinc chloride in tetrahydrofuran and 1-fluoro-4-(2-isocyano-ethyl)-benzene (1.42 g, 6.1 mmol), and purified by flash chromatography (1:3 EtOAc/hex; R$_f$=0.65) to afford 1.5 g (30%) of 3-[{(4-cyano-phenyl)-[2-(4-fluoro-phenyl)-ethylcarbamoyl]-methyl}-(2-cyclohexyl-1-methoxycarbonyl-ethyl)-carbamoyl]-3,4-dihydro-1H-isoquinoline-2-carboxylic acid 9H-fluoren-9-ylmethyl ester (diastereomer A).

The uncyclized product diastereomer A (1.0 g, 1.06 mmol) was dissolved in 8 ml of dichloromethane and 2.0 ml of piperidine. After 1 hour the solvent was removed and the residue placed under vacuum. The crude product was purified by flash chromatography to give 537 mg (62%) of one diastereomer of 2-(4-cyano-phenyl)-2-(3-cyclohexylmethyl-1,4-dioxo-1,3,4,6,11,11a-hexahydro-pyrazino[1,2-b] isoquinolin-2-yl)-N-[2-(4-fluoro-phenyl)-ethyl]-acetamide.

Data for 2-(4-Cyano-phenyl)-2-(3-cyclohexylmethyl-1,4-dioxo-1,3,4,6,11,11a-hexahydro-pyrazino[1,2-b] isoquinolin-2-yl)-N-[2-(4-fluoro-phenyl)-ethyl]-acetamide: R$_f$=0.48 (1:1, EtOAc/hex). $^1$H-NMR (400 MHz, CDCl$_3$): 7.65 (d, 2H, J=8.6), 7.45(d, 2H, J=8.6), 7.3–7.1 (m, 6H), 6.95 (t, 2H, J=8.6), 6.41 (t, 1H, J=5.6 t), 5.40 (d, 1H, J=17.2), 4.89 (s, 1H), 4.22 (dd, 1H, J=12.4, 3.8), 4.13 (d, 1H, J=17.4), 4.06 (dd, 1H, J=9.3, 5.8), 3.54 (m, 2H), 3.26 (dd, 1H, J=16.1, 3.8), 2.95 (t, 1H, J=12.8), 2.76 (t, 2H, J=6.8), 1.7–1.4 (m, 9H), 1.07 (m, 4H), 0.83 (q, 1H, J=12.3), 0.65 (q, 1H, J=12.3).

4-{(3-Cyclohexylmethyl-1,4-dioxo-1,3,4,6,11,11a-hexahydro-pyrazino[1,2-b]isoquinolin-2-yl)-[2-(4-fluoro-phenyl)-ethylcarbamoyl]-methyl}-benzamide (Compound VIII of FIG. 2, structure of FIG. 1, where R$^1$, R$^5$=fused tetrahydroisoquinoline, R$^2$=cyclohexylmethyl, R$^3$=4-carboxamido-phenyl, R$^4$=4-fluorophenyl ethyl)

This compound was prepared by stirring 2-(4-cyano-phenyl)-2-(3-cyclohexylmethyl-1,4-dioxo-1,3,4,6,11,11a-hexahydro-pyrazino[1,2-b]isoquinolin-2-yl)-N-[2-(4-fluoro-phenyl)-ethyl]-acetamide (305 mg, 0.51 mmol) in 10 ml of concentrated sulfuric acid. After 1 hour the solution was poured into 40 g of ice. The ice melted and the white solid was filtered, dried, and the crude product was purified by flash chromatography (1:20 methanol/dichloromethane; R$_f$=0.25) to give 60 mg (20%) of 4-{(3-cyclohexylmethyl-1,4-dioxo-1,3,4,6,11,11a-hexahydro-pyrazino[1,2-b] isoquinolin-2-yl)-[2-4-fluoro-phenyl)-ethylcarbamoyl]-methyl}-benzamide.

Data for 4-{(3-cyclohexylmethyl-1,4-dioxo-1,3,4,6,11, 11a-hexahydro-pyrazino[1,2-b]isoquinolin-2-yl)-[2-(4-fluoro-phenyl)-ethylcarbamoyl]-methyl}-benzamide: MS(APcI): 611 (100, [M]$^+$), 471 (23), 283 (19); exact mass calcd for C$_{36}$H$_{40}$N$_4$O$_4$ ([M]$^+$) 611. $^1$H-NMR (400 MHz, CDCl$_3$); 7.79 (d, 2H, J=8.6), 7.3–7.1 (m, 8H), 6.95 (t, 2H, J=8.6), 6.23 (t, 1H, J=5.6), 5.79 (bs, 2H) 5.40 (d, 1H, J=17.2), 4.89 (s, 1H), 4.22 (dd, 1H, J=12.4, 3.8), 4.13 (d, 1H, J=17.4), 4.06 (dd, 1H, J=9.3, 5.8), 3.54 (m, 2H), 3.26 (dd, 1H, J=16.1, 3.8), 2.95 (t, 1H, J=12.8), 2.76 (t, 2H, J=6.8), 1.7–1.4 (m, 9H), 1.07 (m, 4H), 0.83 (q, 1H, J=12.3), 0.65 (q, 1H, J=12.3).

EXAMPLE 9

2-(3-Benzyl-1,4-dioxo-1,3,4,6,11,11a-hexahydropyrazino[1,2-b]isoquinolin-2-yl)-pentanoic acid [2-(4-hydroxyphenyl)ethyl]-amide (Compound IX of Table 1, structure of Formula A, where R$^1$, R$^5$=fused tetrahydroisoquinoline, R$^2$=phenylmethyl, R$^3$=propyl, R$^4$=4-hydroxy-phenyl-ethyl)

This compound was prepared at room temperature by General Method 4 from L-p-phenylalanine methyl ester HCl salt (0.66 g, 3.1 mmol), butyraldehyde (0.3 ml, 3.3 mmol), Fmoc-L-Tic (1.10 g, 2.76 mmol), 4-(2-isocyanoethyl) phenol, Wang resin ether (0.41 g, 0.29 mmol), triethylamine (430 l, 3.1 mmol), and purified by flash chromatography on SiO$_2$ with a gradient of benzene/acetone (15:1–5:1) to afford two diastereomers. R$_f$ 0.15 (2:8 acetone/benzene).

EXAMPLE 10

2-[3-(4-Hydroxybenzyl)-1,4-dioxo-1,3,4,6,11,11a-hexahydro-pyrazino[1,2-b]isoquinolin-2-yl]-heptanoic acid [2-(4-hydroxyphenyl)-ethyl]amide (Compound X of Table 1, structure of Formula A, where R$^1$, R$^5$=fused tetrahydroisoquinoline, R$^2$=4-hydroxy-phenyl-methyl, R$^3$=pentyl, R$^4$=4-hydroxy-phenyl-ethyl)

This compound was prepared at room temperature by General Method 4 from L-p-tyrosine methyl ester (0.683 g, 3.5 mmol), hexanal (0.39 ml, 3.3 mmol), Fmoc-L-Tic (1.19 g, 2.99 mmol), 4-(2-isocyanoethyl)phenol, Wang resin ether (0.467 g, 0.33 mmol), and purified by flash chromatography on SiO$_2$ with a gradient of benzene/acetone (15:1–5:1) to afford two diastereomers (30 mg). R$_f$ 0.71, 0.65 (4:6 acetone/benzene).

EXAMPLE 11

2-[3-(4-Hydroxy-benzyl)-1,4-dioxo-1,3,4,6,11,11a-hexahydro-pyrazino[1,2-b]isoquinolin-2-yl]-pentanoic acid [2-(4-hydroxyphenyl)-ethylamide (Compound XI of Table 1, structure of Formula A, where R$^1$, R$^5$=fused tetrahydroisoquinoline, R$^2$=4-hydroxy-phenyl-methyl, R$^3$=propyl, R$^4$=4-hydroxy-phenyl-ethyl)

This compound was prepared at room temperature by General Method 4 from L-tyrosine methyl ester (883 mg, 4.5 mmol), butyraldehyde (0.45 ml, 5.0 mmol), Fmoc-L-TIC (1.81 g, 4.5 mmol), 4-(2-isocyanoethyl)phenol, Wang resin ether (643 mg, 0.45 mmol), and purified by flash chromatography on SiO$_2$ with a gradient of benzene/acetone (15:1–5:1) to afford 0.236 g of a mixture of diastereomers. R$_f$ 0.36, 0.29 (1:3 acetone/benzene).

EXAMPLE 12

2-[3-(4-Hydroxybenzyl)-1,4-dioxo-1,3,4,6,11,11a-hexahydropyrazino[1,2-b]isoquinolin-2-yl]-4-methylpentanoic acid [2-(4-hydroxyphenyl)ethyl]amide (Compound XII of Table 1, structure of Formula A, where R$^1$, R$^5$=fused tetrahydroisoquinoline, R$^2$=4-hydroxy-phenyl-methyl, R$^3$=isobutyl, R$^4$=4-hydroxy-phenyl-ethyl)

This compound was prepared at room temperature by General Method 4 from L-tyrosine methyl ester (545 mg, 2.8 mmol), isovaleraldehyde (2.3 mmol), Fmoc-L-TIC (1.06 g, 2.6 mmol), 4-(2-isocyanoethyl)phenol, Wang resin ether (374 mg, 0.26 mmol), and purified by flash chromatography on SiO$_2$ with a gradient of benzene/acetone (15:1–5:1) to afford 64 mg of a mixture of diastereomers. R$_f$ 0.47, 0.43 (3:7 acetone/benzene).

EXAMPLE 13

2-(4-Cyano-phenyl)-2-(3-cyclohexylmethyl-1,4-dioxo-1,3,4,6,11,11a-hexahydro-pyrazino[1,2-]isoquinolin-2-yl)-N-[4-(morpholine-4-carbonyl)-benzyl]-acetamide (Compound XIII of Table 1, structure of Formula A, where R$^1$, R$^5$=fused tetrahydroisoquinoline, R$^2$=cyclohexylmethyl, R$^3$=4-cyanophenyl, R$^4$=(4-(morpholine-4-carbonyl)-benzyl]-methyl)

4-{[2-(4-Cyano-phenyl)-2-(3-cyclohexylmethyl-1,4-dioxo-1,3,4,6,11,11a-hexahydro-pyrazino[1,2-b]isoquinolin-2-yl)-acetylamino]-methyl}-benzoic acid tert-butyl ester (structure of Formula A, where R$^1$, R$^5$=fused tetrahydroisoquinoline, R$^2$=cyclohexylmethyl, R$^3$=4-cyanophenyl, R$^4$=(4-carboxy-phenyl methyl) tert-butyl ester.

To a solution of cyclohexyl-L-alanine methyl ester hydrochloride (222 mg, 1.0 mmol) in ZnCl$_2$ (2.0 mL, 1.0 mmol) were added triethylamine (140 l, 1.0 mmol), 4-cyanobenzaldehyde (133 mg, 1.0 mmol), 4-isocyanomethyl-benzoic acid tert-butyl ester (228 mg, 1.0 mmol), Fmoc-1,2,3,4-tetrahydroisoquinoline-3-carboxylic acid (2 g, 5.0 mmol). The reaction medium was stirred at room temperature for 90 hours, diluted in CH$_2$Cl$_2$ and washed with an ice-cooled solution of saturated aqueous NaHCO$_3$ and brine. The combined organic layers were filtered over a bed of celite and MgSO$_4$, and the solvents were evaporated. The residue was purified by flash chromatography on SiO$_2$ (90 g) with a gradient of hex/EtOAc (4:1–2:1) to afford 311 mg (34%) and 179 mg (19.5%) of each diastereomer A and B.

Data for diastereomer A: MS (APcI): 915.8 (100, [M]$^+$), 708.7 (44), 579.9 (41), 608.0 (33), 661.7 (29), 827.7 (28). HPLC (254 nm): retention time 6.215 (88%); 6.335 (12%). Data for diastereomer B: MS (FIA): 915.8 (100, [M]$^+$), 708.6 (29). HPLC (254 nm): retention time 6.132 (100). HPLC for mixture of diastereomers A and B (254 nm): 6.131 (42.9%), 6.209 (51.9%), 6.332 (5.2%).

The corresponding cyclized products were prepared for each diastereomer (307 mg, 0.34 mmol) and (175.5 mg, 0.19 mmol) using piperidine (0.6 ml and 0.45 ml, respectively) in CH$_2$Cl$_2$ (2.0 ml and 1.5 ml, respectively). The reaction media were stirred under a N$_2$ atmosphere for 4.5 hours, extracted with water and CH$_2$Cl$_2$. The combined organic layers were washed with an ice-cooled saturated NH$_4$Cl solution and brine, dried over MgSO$_4$, and the solvents were evaporated. The residues were purified by flash chromatography on SiO$_2$ (10 g and 5 g, respectively) with a gradient of hex/ EtOAc (4:1–1:1) to afford 110 mg (50%) of 4-{[2-(4-Cyano-phenyl)-2-(3-cyclohexylmethyl-1,4-dioxo-1,3,4, 6,11,11a-hexahydro-pyrazino[1,2-b]isoquinolin-2-yl)-acetylamino]-methyl}-benzoic acid tert-butyl ester (diastereomer A) and 56 mg (45%) of 4-{[2-(4-cyano-phenyl)-2-(3-cyclohexylmethyl-1,4-dioxo-1,3,4,6,11,11a-hexahydro-pyrazino[1,2-b]isoquinolin-2-yl)-acetylamino]-methyl}-benzoic acid tert-butyl ester (diastereomer B).

Data for diastereomer A: MS (APcI): 661.7 (17, [M+H]$^+$), 605.6 (100), 454.5 (92), 311.5 (21). Data for diastereomer B: MS (APcI): 661.7 (20, [M+H]$^+$), 605.6 (100), 454.5 (97), 311.5 (25).

4-{[2-(4-Cyano-phenyl)-2-(3-cyclohexylmethyl-1,4-dioxo-1,3,4,6,11,11a-hexahydro-pyrazino[1,2-b]isoquinolin-2-yl)-acetylamino]-methyl}-benzoic acid (structure of Formula A, where R$^1$, R$^5$=fused 7-hydroxy tetrahydroisoquinoline, R$^2$=cyclohexylmethyl, R$^3$=4-cyanophenyl, R$^4$=(4-carboxy-phenyl methyl).

The above-described cyclized products (diastereomers A and B) were treated with a 1:1 CH$_2$Cl$_2$/CF$_3$CO$_2$H solution according to General Method 3 to afford 114 mg (100%) of 4-{[2-(4-cyano-phenyl)-2-(3-cyclohexylmethyl-1,4-dioxo-1,3,4,6,11,11a-hexahydro-pyrazino[1,2-b]isoquinolin-2-yl)-acetylamino]-methyl}-benzoic acid (diastereomer A) and 62 mg (100%) of 4-{[2-(4-cyano-phenyl)-2-(3-cyclohexylmethyl-1,4-dioxo-1,3,4,6,11,11a-hexahydro-pyrazino[1,2-b]isoquinolin-2-yl)-acetylamino]-methyl}-benzoic acid (diastereomer B).

Data for diastereomer A: MS (APcI, AP$^-$): 717.6 (16, [M–H+CF$_3$CO$_2$H]$^-$), 639.5 (24), 603.5 (100, [M–H]$^-$), 293.4 (60), 308.5 (32). Data for diastereomer B: MS (APcI): 717.4 (18, [M–H+CF$_3$CO$_2$H]$^-$), 639.5 (100), 603.5 (97, [M–H]$^-$), 293.4 (42), 450.4 (35).

To a solution of each above-described t-butyl-deprotected cyclized products (34 mg, 0.05 mmol and 26 mg, 0.04 mmol, respectively) in dry DMF (0.8 ml and 0.5 ml, respectively) were added at 0° C. HOBt (25.2 mg, 0.19 mmol and 16.7 mg, 0.12 mmol, respectively), EDCI (33.1 mg, 0.17 mmol and 24.5 mg, 0.13 mmol, respectively), morpholine (15 l, 0.17 mmol and 10 l, 0.11 mmol respectively), and DIEA (30 l, 0.17 mmol and 20 l, 0.12 mmol, respectively). The reaction media were stirred at room temperature under a N$_2$ atmosphere for 19 hours, and extracted with H$_2$O/EtOAc. The combined organic layers were washed with an ice-cooled saturated NH$_4$Cl solution and brine, dried over MgSO$_4$, and the solvents were evaporated. The residues were purified by flash chromatography on SiO$_2$ (5 g and 5 g, respectively) with a gradient of CH$_2$Cl$_2$/MeOH (100:0–96:4) to afford 21.8 mg (57%) of 2-(4-cyano-phenyl)-2-(3-cyclohexylmethyl-1,4-dioxo-1,3,4,6,11,11a-hexahydro-pyrazino[1,2-b]isoquinolin-2-yl)-N-[4-(morpholine-4-carbonyl)-benzyl]-acetamide (diastereomer A of Compound XIII) and 22.3 mg (77%) of 2-(4-cyano-phenyl)-2-(3-cyclohexylmethyl-1,4-dioxo-1,3,4,6,11,11a-hexahydro-pyrazino[1,2-b]isoquinolin-2-yl)-N-[4-(morpholine-4-carbonyl)-benzyl]-acetamide (diastereomer B of Compound XIII). Epimerization of each previously-isolated diastereomer was observed upon amide coupling of morpholine.

Data for 2-(4-cyano-phenyl)-2-(3-cyclohexylmethyl-1,4-dioxo-1,3,4,6,11,11a-hexahydro-pyrazino[1,2-b]isoquinolin-2-yl)-N-[4-(morpholine-4-carbonyl)-benzyl]-acetamide (diastereomer A of Compound XIII): LC/MS: LC: retention time 3.33 minutes; 674.4 (100, [M+H]$^+$), 364.3 (12), 262.2 (11). $^1$H-NMR (400 MHz, CDCl$_3$): 7.73 (d, 2H, J=8.6), 7.67 (d, 2H, J=8.2), 7.35 (d, 2H, J=8.2), 7.3–7.15 (m, 6H), 6.72 (t, 1H, J=5.7), 5.42 (d, 1H, J=17.2), 5.38 (s, 1H), 4.55–4.4 (m, 1H), 4.48 (t, 1H, J=13.4), 4.37 (dd, 1H, J=3.7, 12.5), 4.17 (d, 1H, J=17.2), 4.03 (dd, 1H, J=3.3, 9.5), 3.75–3.6 (br, 4H), 3.44 (dd, 2H, J=3.8, 16.1), 3.15–3.05 (m, 2H), 1.85–1.8 (m, 3H), 1.60–1.45 (m, 5H), 1.3–1.25 (m, 2H), 1.2–1.15 (m, 1H), 1.15–1.0 (m, 2H), 0.8–0.6 (m, 2H).

Data for 2-(4-cyano-phenyl)-2-(3-cyclohexylmethyl-1,4-dioxo-1,3,4,6,11,11a-hexahydro-pyrazino[1,2-b]isoquinolin-2-yl)-N-[4-(morpholine-4-carbonyl)-benzyl]-acetamide (diastereomer B of Compound XIII): LC/MS: LC: retention time 3.41 minutes; 674.7 (100, [M+H]$^+$), 391.3 (14), 352.3 (12), 262.2 (11). $^1$H-NMR (400 MHz, CDCl$_3$): 7.71 (d, 2H, J=8.4), 7.58 (d, 2H, J=8.2), 7.36 (d, 2H, J=8.2), 7.30 (d, 2H, J=8.1), 7.25–7.15 (m, 4H), 6.86 (t, 1H, J=5.9), 5.45 (d, 1H, J=17.2), 5.12 (s, 1H), 4.55–4.45 (m, 1H), 4.51 (t, 1H, J=4.9), 4.33 (dd, 1H, J=3.8, 12.6), 4.21 (s, 1H), 4.15–4.10 (m, 2H), 3.8–3.6 (br, 3H), 3.5–3.4 (br, 1H), 3.39 (dd, 1H, J=13.4, 16.8), 3.35–3.05 (m, 1H), 1.75–1.65 (m, 9H), 1.60–1.45 (m, 2H), 1.25–1.05 (m, 3H), 0.85–0.8 (m, 1H), 0.65–0.6 (m, 1H).

EXAMPLE 14

4-{[2-(3-Cyclohexylmethyl-1,4-dioxo-1,3,4,6,11,11a-hexahydro-pyrazino[1,2-b]isoquinolin-2-yl)-2-(4-phenoxy-phenyl)-acetylamino]-methyl}-benzoic acid (Compound XIV of Table 1, structure of Formula A, where R$^1$, R$^5$=fused tetrahydroisoquinoline, R$^2$=cyclohexylmethyl, R$^3$=4-phenoxy phenyl, R$^4$=4-carboxy-phenyl methyl)

4-{[2-(3-cyclohexylmethyl-1,4-dioxo-1,3,4,6,11,11a-hexahydro-pyrazino[1,2-b]isoquinolin-2-yl)-2-(4-phenoxy-phenyl)-acetylamino]-methyl}-benzoic acid benzyl ester (structure of Formula A, where R$^1$, R$^5$=fused tetrahydroisoquinoline, R$^2$=cyclohexylmethyl, R$^3$=4-phenoxy phenyl, R$^4$=(4-carboxy-phenyl methyl) benzyl ester).

This compound was prepared by General Method 1 from cyclohexyl-L-alanine methyl ester hydrochloride (220 mg, 1.0 mmol), 4-phenoxybenzaldehyde (196 mg, 1.0 mmol), Fmoc-1,2,3,4-tetrahydroisoquinoline-3-carboxylic acid (395 mg, 1.0 mmol), 4-isocyanomethyl-benzoic acid benzyl ester (250 mg, 1.0 mmol), triethylamine (100 mg, 1.0 mmol), ZnCl$_2$ (2.0 mL, 1.0 mol) and purified by flash chromatography (hex/EtOAc, 3:2) to afford 160 mg (16%) of each diastereomer. Data for diastereomer A: R$_f$ 0.53 (hex/EtOAc, 3:2). Data for diastereomer B: R$_f$ 0.37 (hex/EtOAc, 3:2).

The corresponding cyclized product was prepared for each diastereomer (160 mg, 0.16 mmol) with piperidine (14 mL, 0.16 mmol) and purified by flash chromatography to afford 80 mg (67%) of 4-{[2-(3-cyclohexylmethyl-1,4-dioxo-1,3,4,6,11,11a-hexahydro-pyrazino[1,2-b]isoquinolin-2-yl)-2-(4-phenoxy-phenyl)-acetylamino]-methyl}-benzoic acid benzyl ester (diastereomer A) and 74 mg (61%) of 4-{[2-(3-cyclohexylmethyl-1,4-dioxo-1,3,4,6,11,11a-hexahydro-pyrazino[1,2-b]isoquinolin-2-yl)-2-(4-phenoxy-phenyl)-acetylamino]-methyl}-benzoic acid benzyl ester (diastereomer B).

Data for 4-{[2-(3-cyclohexylmethyl-1,4-dioxo-1,3,4,6,11,11a-hexahydro-pyrazino[1,2-b]isoquinolin-2-yl)-2-(4-phenoxy-phenyl)-acetylamino]-methyl}-benzoic acid benzyl ester (diastereomer A): R$_f$ 0.80 (hex/EtOAc, 1:4). LC/MS: LC: retention time 5.02 minutes; 762.4 (100%, [M+H]$^+$).

Data for 4-{[2-(3-cyclohexylmethyl-1,4-dioxo-1,3,4,6,11,11a-hexahydro-pyrazino[1,2-b]isoquinolin-2-yl)-2-(4-phenoxy-phenyl)-acetylamino]-methyl}-benzoic acid benzyl ester (diastereomer B): R$_f$ 0.46 (hex/EtOAc, 1:4). LC/MS: LC: retention time 4.99 minutes; 762.3 (100%, [M+H]$^+$).

4-{[2-(3-cyclohexylmethyl-1,4-dioxo-1,3,4,6,11,11a-hexahydro-pyrazino[1,2-b]isoquinolin-2-yl)-2-(4-phenoxy-phenyl)-acetylamino]-methy}-benzoic acid (Compound XIV of Table 1, structure of Formula A, where R$^1$, R$^5$=fused tetrahydroisoquinoline, R$^2$=cyclohexylmethyl, R$^3$=4-phenoxy phenyl, R$^4$=4-carboxy-phenyl methyl).

This compound was prepared by General Method 2 from 4-{[2-(3-cyclohexylmethyl-1,4-dioxo-1,3,4,6,11,11a-hexahydro-pyrazino[1,2-b]isoquinolin-2-yl)-2-(4-phenoxy-phenyl)-acetylamino]-methyl}-benzoic acid benzyl ester (15 mg, 0.02 mmol) to afford 12 mg (92%) of Compound XIV (diastereomer A).

Data for Compound XIV (diastereomer A): R$_f$ 0.46 (EtOAc/hex, 4:1). $^1$H-NMR (300 MHz, CD$_3$OD): 8.35 (t, 1H, J=6.0), 7.94 (d, 2H, J=8.2), 7.47 (d, 2H, J=8.5), 7.40 (d, 2H, J=8.0), 7.36–7.31 (m, 2H), 7.19–7.09 (m, 5H), 7.03–6.96 (m, 4H), 5.49 (s, 1H), 5.28 (d, 1H, J=17.0), 4.46 (br s, 2H), 4.41 (dd, 2H, J=12.6, 4.1), 4.19 (d, 1H, J=17.0), 3.96 (dd, 1H, J=9.0, 3.0), 3.38 (dd, 1H, J=16.3, 4.0), 3.15–3.05 (m, 1H), 1.97–1.90 (m, 1H), 1.53–0.8 (br m, 10H), 0.84–0.65 (m, 1H), 0.40–0.60 (m, 1H).

4-{[2-(3-cyclohexylmethyl-1,4-dioxo-1,3,4,6,11,11a-hexahydro-pyrazino[1,2-b]isoquinolin-2-yl)-2-(4-phenoxy-phenyl)-acetylamino]-methyl}-benzoic acid (Compound XIV of Table 1, structure of Formula A, where R$^1$, R$^5$=fused tetrahydroisoquinoline, R$^2$=cyclohexylmethyl, R$^3$=4-phenoxy phenyl, R$^4$=4-carboxy-phenyl methyl).

This compound was prepared by General Method 2 from 4-{[2-(3-cyclohexylmethyl-1,4-dioxo-1,3,4,6,11,11a-hexahydro-pyrazino[1,2-b]isoquinolin-2-yl)-2-(4-phenoxy-phenyl)-acetylamino]-methyl}-benzoic acid benzyl ester (15 mg, 0.02 mmol) to afford 12 mg (92%) of Compound XIV (diastereomer B).

Data for Compound XIV (diastereomer B): R$_f$ 0.28 (EtOAc/hex, 4:1). $^1$H-NMR (300 MHz, acetone-d$_6$): 11.23 (br s, 1H), 7.95 (d, 2H, J=8.2), 7.61 (d, 2H, J=8.8), 7.39–7.44 (m, 4H), 7.24–7.16 (m, 5H), 7.11–7.04 (m, 4H), 5.86 (s, 1H), 5.33 (d, 1H, J=17.0), 4.51 (s, 1H), 4.41 (dd, 1H, J=12.6, 4.12), 4.28 (dd, 1H, J=13.7, 2.7), 4.19 (d, 1H, J=17.0), 3.31 (dd, 1H, J=16.3, 3.7), 3.14–3.04 (m, 1H), 2.86–2.78 (br s, 2H), 1.67–0.85 (br m, 10H), 0.64–0.46 (m, 1H), 0.36–0.19 (m, 1H).

EXAMPLE 15

4-{[2-(3-Benzyl-1,4-dioxo-1,3,4,6,11,11a-hexahydro-pyrazino[1,2-b]isoquinolin-2-yl)-2-(9H-fluoren-3-yl)- acetylamino]-methyl}-benzoic acid (Compound XV of Table 1, structure of Formula A, where $R^1$, $R^5$=fused tetrahydroisoquinoline, $R^2$=phenylmethyl, $R^3$=2-fluorenyl, $R^4$=(4-carboxy-phenyl methyl)

4-{[2-Benzyl-1,4-dioxo-1,3,4,6,11,11a-hexahydro-pyrazino[1,2-b]isoquinolin-2-yl)-2-(9H-fluoren-3-yl)-acetylamino]-methyl}-benzoic acid tert-butyl ester (structure of Formula A, where $R^1$, $R^5$=fused tetrahydroisoquinoline, $R^2$=cyclohexylmethyl, $R^3$=4-cyanophenyl, $R^4$=(4-carboxy-phenyl methyl) tert-butyl ester.

This compound was prepared at room temperature by General Method 1 from cyclohexyl-L-alanine methyl ester hydrochloride (242 mg, 1.1 mmol), 2-fluorene-carboxaldehyde (218 mg, 1.1 mmol), Fmoc-1,2,3,4-tetrahydroisoquinoline-3-carboxylic acid (444 mg, 1.1 mmol), 4-isocyanomethyl-benzoic acid benzyl ester (241 mg, 1.1 mmol), triethylamine (160 l, 1.1 mmol), $ZnCl_2$ (2.4 ml, 1.1 mmol) and purified by flash chromatography on $SiO_2$ with a gradient of hex/EtOAc (9:1–4:1) to afford 0.5 g (46%) of a mixture of diastereomers.

The corresponding cyclized products were prepared from the above-described mixture of diastereomers (122 mg, 0.12 mmol) using piperidine (0.3 ml) in $CH_2Cl_2$ (1.0 ml). The reaction medium was stirred under a $N_2$ atmosphere for 1.5 hour, extracted with an ice-cooled saturated $NH_4Cl$ solution and $CH_2Cl_2$. The combined organic layers were washed with brine, dried over $MgSO_4$, and the solvents were evaporated. The residue was purified by flash chromatography on $SiO_2$ (9 g) with a gradient of hex/EtOAc (19:1–1:2) to afford 12.5 mg (14%) of 4-{[2-Benzyl-1,4-dioxo-1,3,4,6,11,11a-hexahydro-pyrazino[1,2-b]isoquinolin-2-yl)-2-(9H-fluoren-3-yl)-acetylamino]-methyl}-benzoic acid tert-butyl ester (diastereomer A) and 7.6 mg (22%) of 4-{[2-Benzyl-1,4-dioxo-1,3,4,6,11,11a-hexahydro-pyrazino[1,2-b]isoquinolin-2-yl)-2-(9H-fluoren-3-yl)-acetylamino]-methyl}-benzoic acid tert-butyl ester (diastereomer B).

Data for 4-{[2-Benzyl-1,4-dioxo-1,3,4,6,11,11a-hexahydro-pyrazino[1,2-b]isoquinolin-2-yl)-2-(9H-fluoren-3-yl)-acetylamino]-methyl}-benzoic acid tert-butyl ester (diastereomer A): LC/MS: LC: retention time 4.8 minutes; 718.1 (100, $[M+H]^+$), 740.6 (72, $[M+Na]^+$). $^1$H-NMR (300 MHz, $CDCl_3$): 8.05 (d, 2H, J=8.0), 8.00 (d, 2H, J=8.0), 7.95–7.9 (m, 1H), 7.83 (s, 1H), 7.71 (t, 2H, J=8.0), 7.6–7.45 (m, 2H), 7.42 (d, 1H, J=7.7), 7.4–7.2 (m, 9H), 6.44 (t, 1H, J=6.0), 5.96 (s, 1H), 4.95 (d, 1H, J=17.6), 4.75–4.65 (m, 3H), 4.4 (d, 1H, J=17.6), 4.06 (s, 2H), 3.35 (dd, 1H, J=3.6, 15.9), 3.13 (dd, 1H, J=3.6, 13.7), 3.0–2.9 (m, 1H), 2.7–2.6 (m, 2H), 1.72 (s, 9H).

Data for 4-{[2-Benzyl-1,4-dioxo-1,3,4,6,11,11a-hexahydro-pyrazino[1,2-b]isoquinolin-2-yl)-2-(9H-fluoren-3-yl)-acetylamino]-methyl}-benzoic acid tert-butyl ester (diastereomer B): LC/MS: LC: retention time 4.68 minutes; 718.4 (100, $[M+H]^+$), 740.3 (41, $[M+Na]^+$). $^1$H-NMR (300 MHz, $CDCl_3$): 7.92 (d, 2H, J=8.5), 7.85–7.8 (m, 2H), 7.70 (s, 1H), 7.6–7.55 (m, 2H), 7.4–7.3 (m, 2H), 7.35–7.25 (m, 3H), 7.2–7.05 (m, 5H), 7.0–6.95 (m, 1H), 6.98 (d, 1H, J=6.9), 6.80 (d, 1H, J=6.9), 6.5– 6.4 (m, 1H), 5.66 (s, 1H), 5.41 (d, 1H, J 17.3), 4.6–4.55 (m, 3H), 4.15–4.1 (m, 1H), 4.07 (d, 1H, J=17.3), 3.93 (s, 2H), 3.15 (dd, 1H, J=0.6, 1.1), 2.85 (dd, 1H, J=0.6, 1.1), 2.6 (dd, 1H, J=0.6, 1.1), 1.55 (s, 9H).

4-{[2-(3-Benzyl-1,4-dioxo-1,3,4,6,11,11a-hexahydro-pyrazino[1,2-b]isoquinolin-2-yl)-2-(9H-fluoren-3-yl)-acetylamino]-methyl}-benzoic acid (Compound XV of Table 1, structure of Formula A, where $R^1$, $R^5$=fused tetrahydroisoquinoline, $R^2$=phenylmethyl, $R^3$=2-fluorenyl, $R^4$=(4-carboxy-phenyl methyl)

The above-described cyclized products 4-{[2-Benzyl-1, 4-dioxo-1,3,4,6,11,11a-hexahydro-pyrazino[1,2-b] isoquinolin-2-yl)-2-(9H-fluoren-3-yl)-acetylamino]-methyl}-benzoic acid tert-butyl ester (diastereomers A and B) (10.7 mg, 15 mol and 5.9 mg, 8 mol, respectively) were treated with a 1:1 $CH_2Cl_2/CF_3CO_2H$ solution according to General Method 3 to afford 11 mg (100%) of 4-{[2-(3-Benzyl-1,4-dioxo-1,3,4,6,11,11a-hexahydro-pyrazino[1,2-b]isoquinolin-2-yl)-2-(9H-fluoren-3-yl)-acetylamino]-methyl}-benzoic acid (diastereomer A of Compound XV) and 7.2 mg (100%) of 4-{[2-(3-Benzyl-1,4-dioxo-1,3,4,6, 11,11a-hexahydro-pyrazino[1,2-b]isoquinolin-2-yl)-2-(9H-fluoren-3-yl)-acetylamino]-methyl}-benzoic acid (diastereomer B of Compound XV).

Data for 4-{[2-(3-Benzyl-1,4-dioxo-1,3,4,6,11,11a-hexahydro-pyrazino[1,2-b]isoquinolin-2-yl)-2-(9H-fluoren-3-yl)-acetylamino]-methyl}-benzoic acid (diastereomer A of Compound XV): LC/MS: LC: retention time 3.71 minutes; 662.3 (100, $[M+H]^+$), 348.3 (10). $^1$H-NMR (300 MHz, $CDCl_3$): 8.05–7.95 (m, 4H), 7.82 (d, 2H, J=7.7), 7.74 (d, 1H, J=6.9), 7.6–7.5 (m, 4H), 7.45–7.2 (m, 9H), 6.85 (br, 1H), 6.36 (s, 1H), 5.0–4.9 (m, 2H), 4.85 (dd, 1H, J=8.5, 14.3), 4.55–4.45 (m, 2H), 4.10 (s, 2H), 3.39 (dd, 1H, J=3.0, 15.7), 3.1–3.0 (m, 2H), 2.65–2.5 (m, 2H).

Data for 4-{[2-(3-Benzyl-1,4-dioxo-1,3,4,6,11,11a-hexahydro-pyrazino[1,2-b]isoquinolin-2-yl)-2-(9H-fluoren-3-yl)-acetylamino]-methyl}-benzoic acid (diastereomer B of Compound XV): LC/MS: LC: retention time 3.66 minutes; 662.5 (100, $[M+H]^+$). $^1$H-NMR (300 MHz, $CDCl_3$): 8.2–8.1 (m, 5H), 7.97 (d, 1H, J=8.0), 7.88 (d, 1H, J=7.1), 7.75–7.65 (m, 2H), 7.65–7.55 (m, 3H), 7.55–7.35 (m, 4H), 7.35–7.25 (m, 3H), 7.10–7.05 (m, 2H), 6.38 (s, 1H), 5.7 (d, 1H, J=17.0), 5.1–5.05 (m, 1H), 5.05 (d, 1H, J=6.9), 4.55–4.5 (m, 2H), 4.38 (d, 1H, J=16.2), 4.3–4.25 (m, 2H), 3.28 (dd, 1H, J=4.4, 13.7), 3.04 (dd, 1H, J=4.4, 12.6), 2.67 (dd, 1H, J=4.4, 13.5).

EXAMPLE 16

6-[2-(3-Benzyl-6-cyclohexylmethyl-2,5-dioxo-piperazin-1-yl)-2-(4-phenoxy-phenyl)-acetylamino]-hexanoic acid (Compound XVI of Table 1, structure of Formula A, where $R^1$=phenylmethyl, $R^5$=H, $R^2$=cyclohexylmethyl, $R^3$=4-phenoxy-phenyl, $R^4$=6-hexanoic acid)

6-[2-(3-Benzyl-6-cyclohexylmethyl-2,5-dioxo-piperazin-1-yl)-2-(4-phenoxy-phenyl)-acetylamino]-hexanoic acid benzyl ester (structure of Formula A, where $R^1$=phenylmethyl, $R^5$=H, $R^2$=cyclohexylmethyl, $R^3$=4-phenoxy-phenyl, $R^4$=6-hexanoic acid benzyl ester)

This compound was prepared by General Method 1 from cyclohexyl-L-alanine methyl ester hydrochloride (508 mg, 2.5 mmol), 4-phenoxybenzaldehyde (0.44 ml, 2.5 mmol), Fmoc-phenylalanine (970 mg, 6.1 mmol), triethylamine (0.34 ml, 2.4 mmol), 5 ml of 0.5 M zinc chloride in tetrahydrofuran and 6-isocyano-hexanoic acid benzyl ester (577 mg, 2.5 mmol), and purified by flash chromatography (1:3 EtOAc/hex) to afford 0.60 g (25%) of diastereomer A and 0.50 g (20%) of diastereomer B.

Data for diastereomer A: $R_f$=0.42. MS(APcI): 984 (92, $[M]^+$), 555(100), 432 (51), 391 (44); exact mass calcd for $C_{61}H_{66}N_4O_9$ ($[M]^+$) 984. Data for diastereomer B: $R_f$=0.25. MS(APcI): 984 (92, $[M]^+$), 580 (100), 616 (62), 552(37), 432 (73), 391 (54); exact mass calcd for $C_{61}H_{66}N_4O_9$ ($[M]^+$) 984.

The uncyclized product diastereomer A (0.60 g, 0.61 mmol) was dissolved in 8 ml of dichloromethane and 2.0 ml of piperidine. After 1 hour the solvent was removed and placed under vacuum. The crude product was purified by flash chromatography to give 0.30 g of 6-[2-(3-Benzyl-6-cyclohexylmethyl-2,5-dioxo-piperazin-1-yl)-2-(4-phenoxy-phenyl)-acetylamino]-hexanoic acid benzyl ester (67%).

Data for 6-[2-(3-Benzyl-6-cyclohexylmethyl-2,5-dioxo-piperazin-1-yl)-2-(4-phenoxy-phenyl)-acetylamino]- hexanoic acid benzyl ester: $R_f$=0.9 (EtOAc). $^1$H-NMR (400 MHz, CDCl$_3$): 7.4–6.9 (m, 19H), 5.87 (t, 1H, J=5.6), 5.67 (d, 1H, J=3.3), 5.28 (s, 1H), 5.07 (s, 2H), 4.21 (dt, 1H, J=10.4, 3.6), 3.78 (dd, 1H, J=9.3, 5.8), 3.39 (dd, 1H, J=13.5, 3.6), 3.25 (q, 2H, J=6.7), 2.96 (dd, 2H, J=13.5, 10.4), 2.33 (t, 2H, J=7.4), 1.82 (m, 1H), 1.7–1.1 (m, 16H), 0.83 (q, 1H, J=12.3), 0.65 (q, 1H, J=12.3).

The uncyclized product diastereomer B (0.50 g, 0.51 mmol) was dissolved in 8ml of dichloromethane and 2.0 ml of piperidine. After 1 hour the solvent was removed and placed under vacuum. The crude product was purified by flash chromatography to give 0.2 g (54%) of 6-[2-(3-Benzyl-6-cyclohexylmethyl-2,5-dioxo-piperazin-1-yl)-2-(4-phenoxy-phenyl)-acetylamino]-hexanoic acid benzyl ester.

Data for 6-[2-(3-Benzyl-6-cyclohexylmethyl-2,5-dioxo-piperazin-1-yl)-2-(4-phenoxy-phenyl)-acetylamino]-hexanoic acid benzyl ester: Rf=0.31 (1:1 EtOAc/hex). $^1$H-NMR (400 MHz, CDCl$_3$): 7.4–6.9 (m, 19H), 5.87 (t, 1H, J=5.6), 5.67 (d, 1H, J=3.3), 5.09 (s, 1H), 5.07 (s, 2H), 4.21 (dt, 1H, J=10.4, 3.6), 3.78 (dd, 1H, J=9.3, 5.8), 3.32 (dd, 1H, J=13.5, 3.6), 3.25 (q, 2H, J=6.7), 2.96 (dd, 2H, J=13.5, 10.4), 2.31 (t, 2H, J=7.4), 1.7–1.1 (m, 17H), 0.83 (q, 1H, J=12.3), 0.65 (q, 1H, J=12.3)

6-[2-(3-Benzyl-6-cyclohexylmethyl-2,5-dioxo-piperazin-1-yl)-2-(4-phenoxy-phenyl)-acetylamino]-hexanoic acid (Compound XVI of Table 1, structure of Formula A, where $R^1$=phenylmethyl, $R^5$=H, $R^2$=cyclohexylmethyl, $R^3$=4-phenoxy-phenyl, $R^4$=6-hexanoic acid)

This compound was prepared by General Method 2 from 6-[2-(3-benzyl-6-cyclohexylmethyl-2,5-dioxo-piperazin-1-yl)-2-(4-phenoxy-phenyl)-acetylamino]-hexanoic acid benzyl ester(191 mg, 0.17 mmol) to afford 173 mg (100%) of 6-[2-(3-benzyl-6-cyclohexylmethyl-2,5-dioxo-piperazin-1-yl)-2-(4-phenoxy-phenyl)-acetylamino]-hexanoic acid (diastereomer A).

Data for 6-[2-(3-benzyl-6-cyclohexylmethyl-2,5-dioxo-piperazin-1-yl)-2-(4-phenoxy-phenyl)-acetylamino]-hexanoic acid (diastereomer A): $^1$H-NMR (400 MHz, CDCl$_3$): 7.4–6.9 (m, 14H) 5.93 (t, 1H, J=5.6), 5.24 (s, 1H), 4.23 (dt, 1H, J=10.4, 3.6), 3.78 (dd, 1H, J=9.3, 5.8), 3.29 (dd, 1H, J=13.5, 3.6), 3.25 (q, 2H, J=6.7), 2.96 (dd, 2H, J=13.5, 10.4), 2.33 (t, 2H, J=7.4), 1.82 (m, 1H), 1.7–1.1 (m, 16H), 0.83 (q, 1H, J=12.3), 0.65 (q, 1H, J=12.3).

6-[2-(3-Benzyl-6-cyclohexylmethyl-2,5-dioxo-piperazin-1-yl)-2-(4-phenoxy-phenyl)-acetylamino]-hexanoic acid (Compound XVI of Table 1, structure of Formula A, where $R^1$=phenylmethyl, $R^5$=H, $R^2$=cyclohexylmethyl, $R^3$=4-phenoxy-phenyl, $R^4$=6-hexanoic acid)

This compound was prepared by General Method 2 from 6-[2-(3-benzyl-6-cyclohexylmethyl-2,5-dioxo-piperazin-1-yl)-2-(4-phenoxy-phenyl)-acetylamino]-hexanoic acid benzyl ester (133 mg, 0.15 mmol) to afford 119 mg (100%) of 6-[2-(3-benzyl-6-cyclohexylmethyl-2,5-dioxo-piperazin-1-yl)-2-(4-phenoxy-phenyl)-acetylamino]-hexanoic acid (diastereomer B).

Data for 6-[2-(3-benzyl-6-cyclohexylmethyl-2,5-dioxo-piperazin-1-yl)-2-(4-phenoxy-phenyl)-acetylamino]-hexanoic acid (diastereomer B): $^1$H-NMR (400 MHz, CDCl$_3$): 7.4–6.9 (m, 14H) 5.93 (t, 1H, J=5.6), 5.26 (s, 1H), 4.23 (dt, 1H, J=10.4, 3.6), 3.78 (dd, 1H, J=9.3, 5.8), 3.29 (dd, 1H, J=13.5, 3.6), 3.28 (q, 2H, J=6.7), 2.96 (dd, 2H, J=13.5, 10.4), 2.33 (t, 2H, J=7.4), 1.7–1.1 (m, 17H), 0.83 (q, 1H, J=12.3), 0.65 (q, 1H, J=12.3).

EXAMPLE 17

N-[2-(4-Hydroxyphenyl)ethyl]-2-(3-methyl-1,4-dioxo-1,3,4,6,11,11a-hexahydropyrazino[1,2-b]isoquinolin-2-yl)-2-p-tolylacetamide (Compound XVII of Table 1, structure of Formula A, where $R^1$, $R^5$=fused tetrahydroisoquinoline, $R^2$=methyl, $R^3$=tolyl, $R^4$=4-hydroxy-phenyl-ethyl)

This compound was prepared at room temperature by General Method 4 from L-alanine methyl ester HCl salt (0.49 g, 3.5 mmol), p-tolualdehyde (0.41 ml, 3.5 mmol), Fmoc-L-Phe (1.40 g, 3.5 mmol), 4-(2-isocyanoethyl)phenol, Wang resin ether (1 g, 0.7 mmol), triethylamine (488 l, 3.5 mmol), ZnCl$_2$ (477 mg, 3.5 mmol) and purified by flash chromatography on SiO$_2$ with a gradient of benzene/acetone (15:1–5:1) to afford a mixture of two diastereomers (295 mg). $R_f$ 0.30 (4:1 acetone/benzene).

EXAMPLE 18

6-[2-[2-Benzyl-5-(4-nitrobenzyl)-3,6-dioxo-piperazin-1-yl]-2-(3-phenoxyphenyl)acetylamino]hexanoic acid (Compound XVIII of Table 1, structure of Formula A, where $R^1$4-nitro-phenyl-methyl, $R^5$=H, $R^2$=phenylmethyl, $R^3$=2-phenoxy-phenyl, $R^4$=6-hexanoic acid)

This compound was prepared at room temperature by General Method 4 from L-phenylalanine methyl ester HCl salt (0.81 g, 3.76 mmol), m-phenoxybenzaldehyde (0.65 ml, 3.76 mmol), Fmoc-L-p-NO$_2$-Phe (1.66 g, 3.85 mmol), 4-(2-isocyanoethyl)phenol, Wang resin ether (1 g, 0.7 mmol), triethylamine (488 l, 3.5 mmol), ZnCl$_2$ (477 mg, 3.5 mmol) and purified by flash chromatography on SiO$_2$ with a gradient of benzene/acetone (15:1–5:1) to afford two diastereomers (39, 83 mg.). $R_f$ 0.45, 0.25 (4:6 acetone/benzene).

EXAMPLE 19

2-[3-(4-Hydroxybenzyl)-1,4-dioxo-1,3,4,6,11,11a-hexahydro-pyrazino[1,2-b]isoquinolin-2-yl]-N-[2-(4-hydroxyphenyl)ethyl]acetamide (Compound XIX of Table 1, structure of Formula A, where $R^1$, $R^5$=fused tetrahydroisoquinoline, $R^2$=4-hydroxy-phenyl-methyl, $R^3$=H, $R^4$=4-hydroxy-phenyl-ethyl)

This compound was prepared at room temperature by General Method 4 from L-tyrosine methyl ester HCl salt (0.72 g, 3.7 mmol), formalin solution (37% formaldehyde in H$_2$O, 0.8 ml, 9.9 mmol), Fmoc-L-Tic (1.23 g, 3.1 mmol), 4-(2-isocyanoethyl)phenol, Wang resin ether (0.54 g, 0.38 mmol), and purified by flash chromatography on SiO$_2$ with a gradient of benzene/acetone (15:1–5:1) to afford a single diastereomer (52 mg.) $R_f$ 0.28 (35:65 acetone/benzene).

EXAMPLE 20

2-[3-(4-Hydroxybenzyl)-1,4-dioxo-1,3,4,6,11,11a-hexahydro-pyrazino[1,2-b]isoquinolin-2-yl]-N-[2-(4-hydroxyphenyl)ethyl]butyramide (Compound XX of Table 1, structure of Formula A, where $R^1$, $R^5$=fused tetrahydroisoquinoline, $R^2$=4-hydroxy-phenyl-methyl, $R^3$=ethyl, $R^4$=4-hydroxy-phenyl-ethyl)

This compound was prepared at room temperature by General Method 4 from L-tyrosine methyl ester HCl salt (0.56 g, 2.9 mmol), propionaldehyde (0.4 ml, 5.5 mmol), Fmoc-L-Tic (1.16 g, 2.9 mmol), 4-(2-isocyanoethyl)phenol, Wang resin ether (0.40 g, 0.28 mmol) to yield 0.19 g crude product. This was purified by flash chromatography on SiO$_2$ with a gradient of benzene/acetone (15:1–5:1) to afford two diastereomers (65 mg). $R_f$ 0.39, 0.33 (3:7 acetone/benzene, eluted twice).

EXAMPLE 21

2-(4-Cyano-phenyl)-2-(3-cyclohexylmethyl-1,4-dioxo-1,3,4,6,11,11a-hexahydro-pyrazino[1,2-b]isoquinolin-2-yl)-N-[2-(4-methoxy-phenyl)-ethyl]-acetamide (Compound XXI of Table 1, structure of Formula A, where $R^1$, $R^5$=fused tetrahydroisoquinoline, $R^2$=cyclohexylmethyl, $R^3$=4-cyano-phenyl, $R^4$=4-methoxyphenyl ethyl)

This compound was prepared by General Method 1 from L-cyclohexylalanine methyl ester hydrochloride salt (317 mg, 1.9 mmol), 4-cyanobenzaldehyde (235 mg, 1.8 mmol), Fmoc-L-1,2,3,4-tetrahydroisoquinoline-3-carboxylic acid (759 mg, 1.9 mmol), triethylamine (1.9 mmol), 4 ml of 0.5 M zinc chloride in tetrahydrofuran and 1-(2-isocyanoethyl)-4-methoxy-benzene (305 g, 1.9 mmol), and purified by flash chromatography (1:3 EtOAc/hex) to afford 0.40 g of diastereomer A.

Data for diastereomer A: $R_f$=0.35 (1:3, EtOAc/hex). MS(APcI) 858 (93, [M]⁻), 636 (59), 604 (100), 429 (47); exact mass calcd for $C_{53}H_{53}N_4O_7$ (M⁻) 858.

The uncyclized product diastereomer A (194 mg, 0.23 mmol) was dissolved in 8 ml of dichloromethane and 2.0 ml of piperidine. After 1 hour the solvent was removed and the residue placed under vacuum. The crude product was purified by flash chromatography to give 72 mg (56%) of 2-(4-cyano-phenyl)-2-(3-cyclohexylmethyl-1,4-dioxo-1,3,4,6,11,11a-hexahydro-pyrazino[1,2-b]isoquinolin-2-yl)-N-[2-(4-methoxy-phenyl)-ethyl]-acetamide (diastereomer A) and 14 mg (10%) of 2-(4-cyano-phenyl)-2-(3-cyclohexylmethyl-1,4-dioxo-1,3,4,6,11,11a-hexahydro-pyrazino[1,2-b]isoquinolin-2-yl)-N-[2-(4-methoxy-phenyl)-ethyl]-acetamide (diastereomer B).

Data for 2-(4-cyano-phenyl)-2-(3-cyclohexylmethyl-1,4-dioxo-1,3,4,6,11,11a-hexahydro-pyrazino[1,2-b]isoquinolin-2-yl)-N-[2-(4-methoxy-phenyl)-ethyl]-acetamide (diastereomer A): $R_f$=0.17 (1:1, EtOAc/hex). ¹H-NMR (400 MHz, CDCl₃): 7.61 (d, 2H, J=8.3 Hz), 7.40 (d, 2H, J=8.5), 7.15 (4H, m), 7.03 (d, 2H, J=8.5 Hz), 6.37 (d, 2H, J=8.5 Hz) 6.36 (t, 1H, J=5.8 Hz), 5.40 (d, 1H, J=17.3Hz), 4.91 (1H, s), 4.22 (dd, 1H, J=12.4, 3.8 Hz), 4.13 (d, 1H, J=17.4 Hz), 4.06 (dd, 1H, J=9.3, 5.8 Hz), 3.76 (3H, s), 3.54 (2H, m), 3.26 (dd, 1H, J=16.1, 3.8 Hz), 2.95 (t, 1H, J=12.8 Hz ), 2.76 (t, 2H, J=6.8 Hz), 1.7–1.4 (9H, m), 1.12 (4H, m), 0.83 (q, 1H, J=12.3 Hz), 0.65 (q, 1H, J=12.3 Hz). MS(APcI) 606(49, [M]⁺), 455 (100), 135 (43); exact mass calcd for $C_{37}H_{41}N_4O_4$ (M⁺) 606.

Data for 2-(4-cyano-phenyl)-2-(3-cyclohexylmethyl-1,4-dioxo-1,3,4,6,11,11a-hexahydro-pyrazino[1,2-b]isoquinolin-2-yl)-N-[2-(4-methoxy-phenyl)-ethyl]-acetamide (diastereomer B): $R_f$= 0.12 (1:1, EtOAc/hex). ¹H-NMR (400 MHz, CDCl₃): 7.61 (d, 2H, J=8.3 Hz), 7.40 (d, 2H, J=8.5), 7.15 (4H, m), 7.03 (d, 2H, J=8.5 Hz), 6.37 (d, 2H, J=8.5 Hz), 5.91 (t, 1H, J=5.8 Hz), 5.40 (d, 1H, J=17.3Hz), 5.18 (1H, s), 4.22 (dd, 1H, J=12.4, 3.8 Hz), 4.13 (d, 1H, J=17.4 Hz), 4.06 (dd, 1H, J=9.3, 5.8 Hz), 3.76 (3H, s), 3.54 (2H, m), 3.26 (dd, 1H, J=16.1, 3.8 Hz), 2.95 (t, 1H, J=12.8 Hz), 2.76 (t, 2H, J=6.8 Hz), 1.79 (2H, m) 1.70–1.4 (7H, m), 1.12 (2H, m), 0.72 (2H, m). MS(APcI): 606(83, [M]⁺), 455 (100), 135 (76); exact mass calcd for $C_{37}H_{41}N_4O_4$ (M⁺) 606.

EXAMPLE 22

2-(4-Cyano-phenyl)-2-(3-cyclohexylmethyl-1,4-dioxo-1,3,4,6,11,11a-hexahydro-pyrazino[1,2-b]isoquinolin-2-yl)-N-[4-(piperidine-1-carbonyl)-benzyl]-acetamide (Compound XXII of Table 1, structure of Formula A, where $R^1$, $R^5$=fused tetrahydroisoquinoline, $R^2$=cyclohexylmethyl, $R^3$=4-cyanophenyl, $R^4$=([4-(piperidine-1-carbonyl)-benzyl]-methyl).

4-{[2-(4-Cyano-phenyl)-2-(3-cyclohexylmethyl-1,4-dioxo-1,3,4,6,11,11a-hexahydro-pyrazino[1,2-b]isoquinolin-2-yl)-acetylamino]-methyl}-benzoic acid tert-butyl ester (structure of Formula A, where $R^1$, $R^5$=fused tetrahydroisoquinoline, $R^2$=cyclohexylmethyl, $R^3$=4-cyanophenyl, $R^4$=(4-carboxy-phenyl methyl) tert-butyl ester.)

This compound was prepared by General Method 1 from cyclohexyl-L-alanine methyl ester hydrochloride (58 mg, 0.26 mmol), 4-cyanobenzaldehyde (34 mg, 0.26 mmol), Fmoc- 1,2,3,4-tetrahydroisoquinoline-3-carboxylic acid (104 mg, 0.26 mmol), 4-isocyanomethyl-benzoic acid tert-butyl ester (56 mg, 0.26 mmol), triethylamine (37 l, 0.26 mmol), ZnCl₂ (520 L, 0.26 mmol) and purified by flash chromatography on SiO₂ with a gradient of hex/EtOAc (9:1–4:1) to afford 73 mg (31%) and 69 mg (29%) of each diastereomer A and B.

Data for diastereomer A: LC/MS: LC: retention time 3.49 minutes; 937 (100), 915 (35, [M-H]⁻), 708 (80, [M-HNCH₂-Phe-CO₂tBu]⁻).

Data for diastereomer B: LC/MS: LC: retention time 3.45 minutes; 937 (25), 915 (35, [M-H]⁻), 709 (100, [M-HNCH₂-Phe-CO₂tBu]⁻), 730 (11).

The corresponding cyclized products were prepared for each diastereomer (67 mg, 73 mol) and (63 mg, 69 mol) using piperidine (0.3 ml each) in CH₂Cl₂ (1.0 ml each). The reaction media were stirred under a N₂ atmosphere for 4 hours, extracted with water and CH₂Cl₂. The combined organic layers were washed with an ice-cooled saturated NH₄Cl solution and brine, dried over MgSO₄, and the solvents were evaporated. The residues were purified by flash chromatography on SiO₂ (5 g each) with a gradient of hex/EtOAc (4:1–1:1) to afford 25 mg (52%) of 4-{[2-(4-cyano-phenyl)-2-(3-cyclohexylmethyl-1,4-dioxo-1,3,4,6,11,11a-hexahydro-pyrazino[1,2-b]isoquinolin-2-yl)-acetylamino]-methyl}-benzoic acid tert-butyl ester (diastereomer A) and 16 mg (35%) of 4-{[2-(4-cyano-phenyl)-2-(3-cyclohexylmethyl-1,4-dioxo-1,3,4,6,11,11a-hexahydro-pyrazino[1,2-b]isoquinolin-2-yl)-acetylamino]-methyl}-benzoic acid tert-butyl ester (diastereomer B).

Data for diastereomer A: MS (APcI): 661.67 (45, [M+H]⁺), 605.63 (100, [M+H-tBu]⁺), 454.59 (64), 428.62 (29), 408.60 (14). Data for diastereomer B: MS (APcI): 661.68 (37, [M+H]⁺), 605.63 (100, [M+H-tBu]⁺), 454.59 (63), 534.65 (29), 428.62 (28), 408.60 (13).

4-{[2-(4-Cyano-phenyl)-2-(3-cyclohexylmethyl-1,4-dioxo-1,3,4,6,11,11a-hexahydro-pyrazino[1,2-b]isoquinolin-2-yl)-acetylamino]-methyl}-benzoic acid (structure of Formula A, where $R^1$, $R^5$=fused 7-hydroxy tetrahydroisoquinoline, $R^2$=cyclohexylmethyl, $R^3$=4-cyanophenyl, $R^4$=(4-carboxy-phenyl methyl).

The above-described cyclized products 4-{[2-(4-cyano-phenyl)-2-(3-cyclohexylmethyl-1,4-dioxo-1,3,4,6,11,11a-hexahydro-pyrazino[1,2-b]isoquinolin-2-yl)-acetylamino]-methyl}-benzoic acid tert-butyl ester (diastereomers A and B) were treated with a 1:1 CH₂Cl₂/CF₃CO₂H solution according to General Method 3 to afford 27 mg (100%) of 4-{[2-(4-cyano-phenyl)-2-(3-cyclohexylmethyl-1,4-dioxo-1,3,4,6,11,11a-hexahydro-pyrazino[1,2-b]isoquinolin-2-yl)-acetylamino]-methyl}-benzoic acid (diastereomer A) and 35 mg (100%) of 4-{[2-(4-cyano-phenyl)-2-(3-cyclohexylmethyl-1,4-dioxo-1,3,4,6,11,11a-hexahydro-pyrazino[1,2-b]isoquinolin-2-yl)-acetylamino]-methyl}-benzoic acid (diastereomer B).

Data for diastereomer A: MS (APcI): 605.62 (42, [M+H]⁺), 454.56 (100), 428.59 (95), 311.52 (46). Data for diastereomer B: MS (APcI): 605.62 (22, [M+H]⁺), 454.56 (67), 428.59 (100), 311.53 (41).

2-(4-Cyano-phenyl)-2-(3-cyclohexylmethyl-1,4-dioxo-1,3,4,6,11,11a-hexahydro-pyrazino[1,2-b]isoquinolin-2-yl)-N-[4-(piperidine-1-carbonyl)-benzyl]-acetamide (Compound XXII of Table 1, structure of Formula A, where $R^1$, $R^5$=fused tetrahydroisoquinoline, $R^2$=cyclohexylmethyl, $R^3$=4-cyanophenyl, $R^4$=([4-(piperidine-1-carbonyl)-benzyl]-methyl).

To a solution of each above-described t-butyl-deprotected cyclized products 4-{[2-(4-cyano-phenyl)-2-(3-cyclohexylmethyl-1,4-dioxo-1,3,4,6,11,11a-hexahydro-pyrazino[1,2-b]isoquinolin-2-yl)-acetylamino]-methyl}- benzoic acid (diastereomers A and B) (23.3 mg, 0.04 mmol and 35.8 mg, 0.06 mmol, respectively) in dry DMF (0.3 ml and 0.8 ml, respectively) were added at 0° C. HOBt (22.8 mg, 0.17 mmol and 28.2 mg, 0.21 mmol, respectively), EDCI (24.2 mg, 0.13 mmol and 37.7 mg, 0.20 mmol, respectively), piperidine (12 l, 0.12 mmol and 18 l, 0.18 mmol respectively), and DIEA (25 l, 0.15 mmol and 31 l, 0.18 mmol, respectively). The reaction media were stirred at room temperature under a $N_2$ atmosphere for 20 hours, and extracted with $H_2O$/EtOAc. The combined organic layers were washed with an ice-cooled saturated $NH_4Cl$ solution and brine, dried over $MgSO_4$, and the solvents were evaporated. The residues were purified by flash chromatography on $SiO_2$ (2 g and 5 g, respectively) with a gradient of $CH_2Cl_2$/MeOH (100:0– 95:5) to afford 11.7 mg (45%) of 2-(4-cyano-phenyl)-2-(3-cyclohexylmethyl-1,4-dioxo-1,3,4,6,11,11a-hexahydro-pyrazino[1,2-b]isoquinolin-2-yl)-N-[4-(piperidine-1-carbonyl)-benzyl]-acetamide (diastereomer A of Compound XXII) and 10.1 mg (25%) of 2-(4-cyano-phenyl)-2-(3-cyclohexylmethyl-1,4-dioxo-1,3,4,6,11,11a-hexahydro-pyrazino[1,2-b]isoquinolin-2-yl)-N-[4-(piperidine-1-carbonyl)-benzyl]-acetamide (diastereomer B of Compound XXII). Epimerization of each previously-isolated diastereomer was observed upon amide coupling of piperidine.

Data for 2-(4-cyano-phenyl)-2-(3-cyclohexylmethyl-1,4-dioxo-1,3,4,6,11,11a-hexahydro-pyrazino[1,2-b]isoquinolin-2-yl)-N-[4-(piperidine-1-carbonyl)-benzyl]-acetamide (diastereomer A of Compound XXII): MS (APcI): 672.7 (100, [M+H]$^+$), 219.4 (36), 311.5 (12), 362.5 (11), 428.5 (11). $^1$H-NMR (300 MHz, CDCl$_3$): 7.71 (d, 2H, J=4.1), 7.60 (d, 2H, J=1.9), 7.34–7.15 (m, 8H), 6.96 (t, 1H, J=6.0), 5.45 (d, 1H, J=17.0), 5.14 (s, 1H), 4.86 (t, 1H, J=16.5), 4.49 (d, 1H, J=5.8), 4.32 (dd, 1H, J=3.8, 12.4), 4.2–4.1 (br, 1H), 4.18 (d, 1H, J=17.3), 3.68 (br, 1H), 3.4–3.35 (br, 1H), 3.38 (dd, 1H, J=4.1, 16.5), 3.4–3.35 (br, 1H), 3.1–3.0 (m, 1H), 1.7–1.4 (m, 14H), 1.25–1.1 (m, 4H), 0.9–0.8 (m, 1H), 0.7–0.6 (m, 1H).

Data for 2-(4-cyano-phenyl)-2-(3-cyclohexylmethyl-1,4-dioxo-1,3,4,6,11,11a-hexahydro-pyrazino[1,2-b]isoquinolin-2-yl)-N-[4-(piperidine-1-carbonyl)-benzyl]-acetamide (diastereomer B of Compound XXII): MS (APcI): 672.7 (100, [M+H]$^+$), 219.4 (42), 362.5 (16), 311.5 (14), 428.5 (11). $^1$H-NMR (300 MHz, CDCl$_3$): 7.74 (d, 2H, J=6.3), 7.68 (d, 2H, J=8.5), 7.33 (d, 1H, J=8.5), 7.3–7.15 (m, 7H), 6.67 (t, 1H, J=5.8), 5.43 (d, 1H, J=17.0), 5.41 (s, 1H), 4.55–4.4 (m, 1H), 4.49 (t, 1H, J=6.3), 4.37 (dd, 1H, J=3.9, 12.4), 4.18 (d, 1H, J=17.3), 4.05 (dd, 1H, J=3.0, 9.3), 3.69 (br, 1H), 3.45 (dd, 1H, J=3.6, 15.9), 3.32 (br, 1H), 3.15–3.05 (m, 1H), 1.7–1.4 (m, 2H), 1.25–1.1 (m, 13H), 0.9–0.8 (m, 1H), 0.7–0.6 (m, 1H).

EXAMPLE 23

2-(4-Cyano-phenyl)-2-(3-cyclohexylmethyl-1,4-dioxo-octahydro-pyrido[1,2-a]pyrazin-2-yl)-N-[2-(4-hydroxy-phenyl)-ethyl]-acetamide (Compound XXIII of Table 1, structure of Formula A, where $R^1$, $R^5$=fused piperidine, $R^2$=cyclohexylmethyl, $R^3$=4-cyanophenyl, $R^4$=4-hydroxyphenyl ethyl).

N-[2-(4-Benzyloxy-phenyl)-ethyl]-2-(4-cyano-phenyl)-2-(3-cyclohexylmethyl-1,4-dioxo-octahydro-pyrido [1,2-a] pyrazin-2-yl)-acetamide (structure of Formula A, where $R^1$, $R^5$=fused piperidine, $R^2$=cyclohexylmethyl, $R^3$=4-cyanophenyl, $R^4$=(4-benzyloxy-phenyl)-ethyl).

This compound was prepared by General Method 1 from cyclohexyl-L-alanine methyl ester hydrochloride (185 mg, 0.8 mmol), 4-cyanobenzaldehyde (110 mg, 0.8 mmol), Fmoc-L-pipecolic acid (294 mg, 0.8 mmol), 4-(2-isocyano-ethyl)-phenol benzyl ether (200 mg, 0.8 mmol), triethylamine (85 mg, 0.8 mol), ZnCl$_2$ (1.6 mL, 0.8 mol) and purified by flash chromatography (hex/EtOAc, 3:2) to afford 187 mg (25%) of diastereomer A and 167 mg (22%) of diastereomer B.

The corresponding cyclized product was prepared from diastereomer A (187 mg, 0.22 mmol) with piperidine (18 mL, 0.22 mmol) and purified by flash chromatography to afford 44 mg (33%) of N-[2-(4-benzyloxy-phenyl)-ethyl]-2-(4-cyano-phenyl)-2-(3-cyclohexylmethyl-1,4-dioxo-octahydro-pyrido[1,2-a]pyrazin-2-yl)-acetamide as a single diastereomer.

The corresponding cyclized product was prepared from diastereomer B (167 mg, 0.18 mmol) with piperidine (16 mL, 0.18 mmol) and purified by flash chromatography to afford 26 mg (22%) of N-[2-(4-benzyloxy-phenyl)-ethyl]-2-(4-cyano-phenyl)-2-(3-cyclohexylmethyl-1,4-dioxo-octahydro-pyrido[1,2-a]pyrazin-2-yl)-acetamide as a single diastereomer.

2-(4-Cyano-phenyl)-2-(3-cyclohexylmethyl-1,4-dioxo-octahydro-pyrido[1,2-a]pyrazin-2-yl)-N-[2-(4-hydroxy-phenyl)-ethyl]-acetamide (Compound XXIII of Table 1, structure of Formula A, where $R^1$, $R^5$=fused piperidine, $R^2$=cyclohexylmethyl, $R^3$=4-cyanophenyl, $R^4$=4-hydroxyphenyl ethyl).

This compound was prepared by General Method 2 from N-[2-(4-benzyloxy-phenyl)-ethyl]-2-(4-cyano-phenyl)-2-(3-cyclohexylmethyl-1,4-dioxo-octahydro-pyrido[1,2-a] pyrazin-2-yl)-acetamide (70 mg, 0.11 mmol) to afford 15 mg (25%) of 2-(4-cyano-phenyl)-2-(3-cyclohexylmethyl-1,4-dioxo-octahydro-pyrido[1,2-a]pyrazin-2-yl)-N-[2-(4-hydroxy-phenyl)-ethyl]-acetamide.

Data for 2-(4-cyano-phenyl)-2-(3-cyclohexylmethyl-1,4-dioxo-octahydro-pyrido[1,2-a]pyrazin-2-yl)-N-[2-(4-hydroxy-phenyl)-ethyl]-acetamide: $R_f$ 0.23 (EtOAc/hex, 4:1). $^1$H-NMR (300 MHz, CD$_3$OD): 8.16 (s, 1H), 7.78 (d, 2H, J=8.5), 7.60 (d, 2H, J=8.2), 7.51 (t, 1H, J=5.5), 7.0 (d, 2H, J=8.5), 6.72 (d, 2H, J=8.5), 5.56 (s, 1H), 4.52–4.46 (m, 1H), 4.20 (dd, 1H, J=8.9, 3.1), 3.93 (dd, 1H, J=12.2, 2.9), 3.50–3.33 (m, 2H), 2.68 (t, 2H, J=7.0), 2.61–2.52 (m, 1H), 2.19–2.15 (m, 1H), 1.98–1.90 (m, 1H), 1.70–0.9 (br m, 15H), 0.75–0.69 (m, 1H), 0.50–0.43 (m, 1H).

What is claimed is:
1. A compound of the formula:

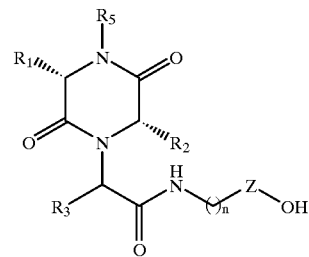

Wherein $R^1$ is aralkyl or cycloalkyl;

$R^2$ is cycloalkylmethyl, alkyl, or aralkyl;

$R^3$ is hydrogen, alkyl, substituted phenyl or fluorenyl;

$R^5$ is hydrogen or $R^1$ and $R^5$ taken together forming a tetrahydroisoquinoline ring, a piperidine ring, a substituted tetrahydroisoquinoline ring or a substituted piperidine ring;

when n=1,

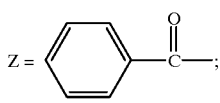

when n=2,

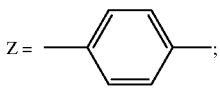

when n=5,

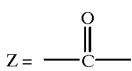

and the pharmaceutically acceptable salts thereof.

2. A compound according to claim 1, by the name of 2-(4-cyano-phenyl)-2-(3-cyclohexylmethyl-1,4-dioxo-octahydro-pyrido[1,2-a]pyrazin-2-yl)-N-[2-(4-hydroxy-phenyl)-ethyl]-acetamide having the following structural formula:

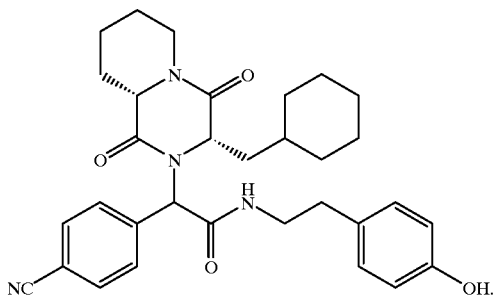

3. A compound by the name of 2-(4-cyano-phenyl)-2-(3-cyclohexylmethyl-8-hydroxy-1,4-dioxo-1,3,4,6,11,11a-hexahydro-pyrazino[1,2-b]isoquinolin-2-yl)-N-[2-(4-hydroxy-phenyl)-ethyl]-acetamide having the following structural formula:

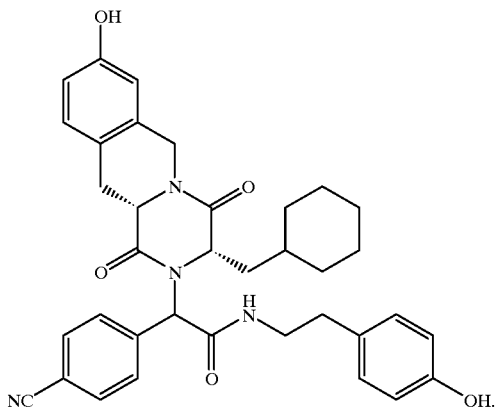

4. A compound by the name of 2-(4-cyano-phenyl)-2-(3-cyclohexylmethyl-1,4-dioxo-1,3,4,6,11,11a-hexahydro-pyrazino[1,2-b]isoquinolin-2-yl)-N-[2-(4-hydroxy-phenyl)-ethyl]-acetamide having the following structural formula:

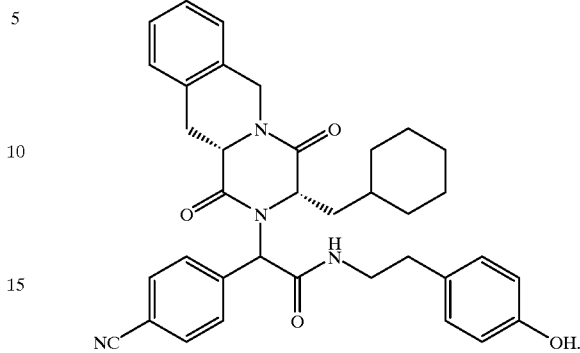

5. A compound by the name of 2-(4-cyano-phenyl)-2-(3-cyclohexylmethyl-1,4-dioxo-1,3,4,6,11,11a-hexahydro-pyrazino[1,2-b]isoquinolin-2-yl)-N-[2-(3-hydroxy-phenyl)-ethyl]-acetamide having the following structural formula:

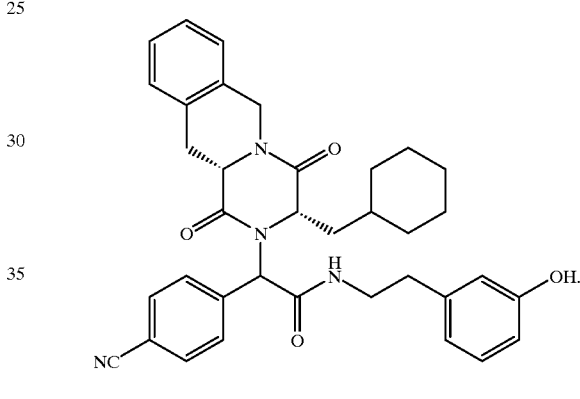

6. A compound by the name of 2-(3-benzyl-1,4-dioxo-1,3,4,6,11,11a-hexahydro-pyrazino[1,2-b]isoquinolin-2-yl)-2-(4-cyano-phenyl)-N-[2-(4-hydroxy-phenyl)-ethyl]-acetamide having the following structural formula:

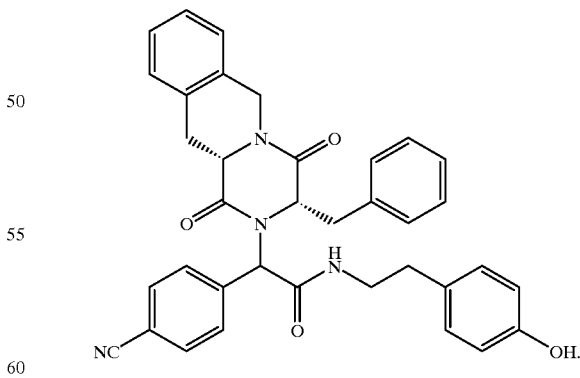

7. A compound by the name of N-[2-(4-hydroxy-phenyl)-ethyl]-2-(3-isobutyl-1,4-dioxo-1,3,4,6,11,11a-hexahydro-pyrazino[1,2-b]isoquinolin-2-yl)-2-(4-nitro-phenyl)-acetamide having the following structural formula:

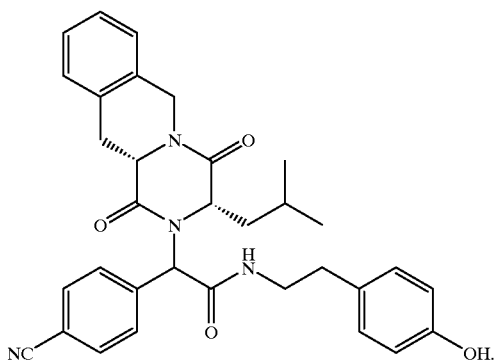

8. A compound by the name of 2-(3-benzyl-6-cyclohexylmethyl-2,5-dioxo-piperazin-1-yl)-N-[2-(4-hydroxy-phenyl)-ethyl]-2-(4-nitro-phenyl)-acetamide having the following structural formula:

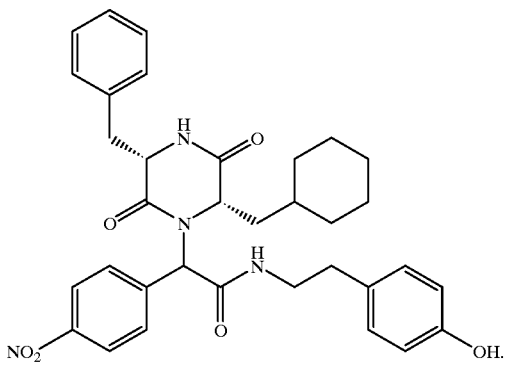

9. A compound by the name of 2-(4-cyano-phenyl)-N-[2-(4-hydroxy-phenyl)-ethyl]-2-(3-isobutyl-1,4-dioxo-1,3,4,6,11,11a-hexahydro-pyrazino[1,2-b]isoquinolin-2-yl)-acetamide having the following structural formula:

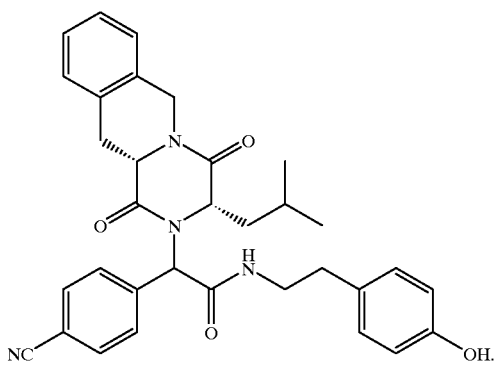

10. A compound by the name of 2-(3-benzyl-1,4-dioxo-1,3,4,6,11,11a-hexahydro-pyrazino[1,2-b]isoquinolin-2-yl)-pentanoic acid [2-(4-hydroxy-phenyl)-ethyl]-amide having the following structural formula:

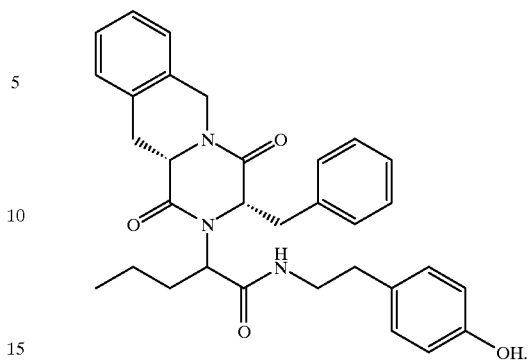

11. A compound by the name of 2-[3-(4-hydroxy-benzyl)-1,4-dioxo-1,3,4,6,11,11a-hexahydro-pyrazino[1,2-b]isoquinolin-2-yl]-heptanoic acid [2-(4-hydroxy-phenyl)-ethyl]-amide having the following structural formula:

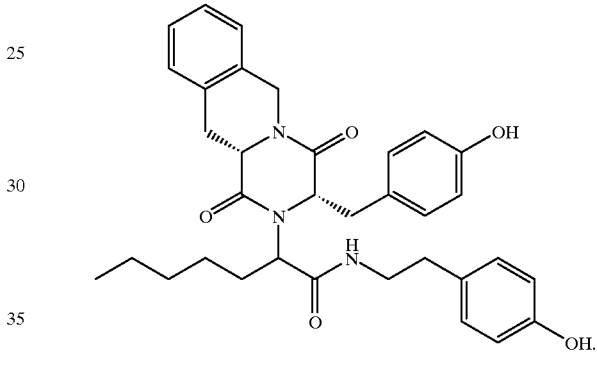

12. A compound by the name of 2-[3-(4-hydroxy-benzyl)-1,4-dioxo-1,3,4,6,11,11a-hexahydro-pyrazino[1,2-b]isoquinolin-2-yl]-pentanoic acid [2-(4-hydroxy-phenyl)-ethyl]-amide having the following structural formula:

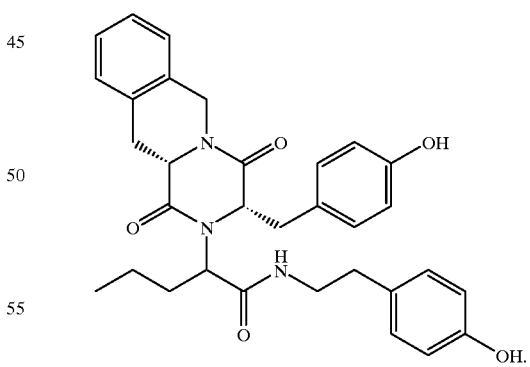

13. A compound by the name of 2-[3-(4-hydroxy-benzyl)-1,4-dioxo-1,3,4,6,11,11a-hexahydro-pyrazino[1,2-b]isoquinolin-2-yl]-4-methyl-pentanoic acid [2-(4-hydroxy-phenyl)-ethyl]-amide having the following structural formula:

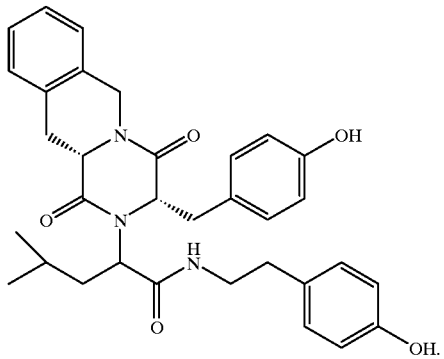

14. A compound by the name of 4-{[2-(3-cyclohexylmethyl-1,4-dioxo-1,3,4,6,11,11a-hexahydro-pyrazino[1,2-b]isoquinolin-2-yl)-2-(4-phenoxy-phenyl)-acetylamino]-methyl}-benzoic acid having the following structural formula:

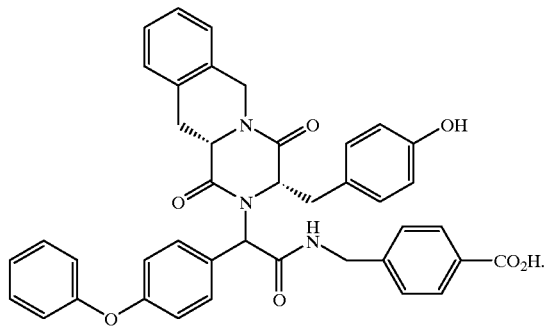

15. A compound by the name of 4-{[2-(3-benzyl-1,4-dioxo-1,3,4,6,11,11a-hexahydro-pyrazino[1,2-b]isoquinolin-2-yl)-2-(9H-fluoren-3-yl)-acetylamino]-methyl}-benzoic acid having the following structural formula:

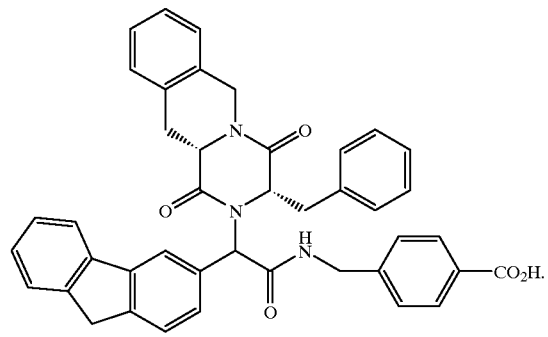

16. A compound by the name of 6-[2-(3-benzyl-6-cyclohexylmethyl-2,5-dioxo-piperazin-1-yl)-2-(4-phenoxy-phenyl)-acetylamino]-hexanoic acid having the following structural formula:

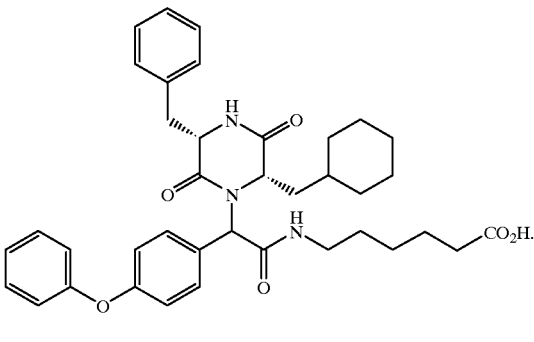

17. A compound by the name of N-[2-(4-hydroxy-phenyl)-ethyl]-2-(3-methyl-1,4-dioxo-1,3,4,6,11,11a-hexahydro-pyrazino[1,2-b]isoquinolin-2-yl)-2-p-tolyl-acetamide having the following structural formula:

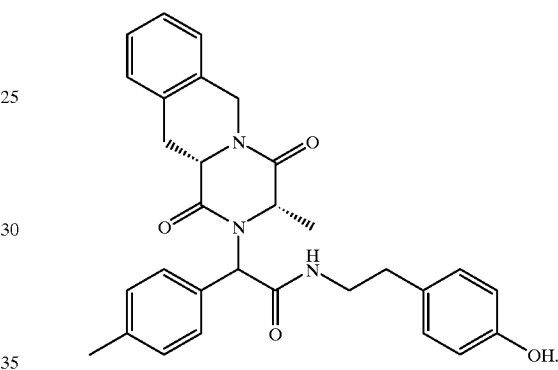

18. A compound by the name of 6-[2-[2-benzyl-5-(4-nitro-benzyl)-3,6-dioxo-piperazin-1-yl]-2-(4-phenoxy-phenyl)-acetylamino]-hexanoic acid having the following structural formula:

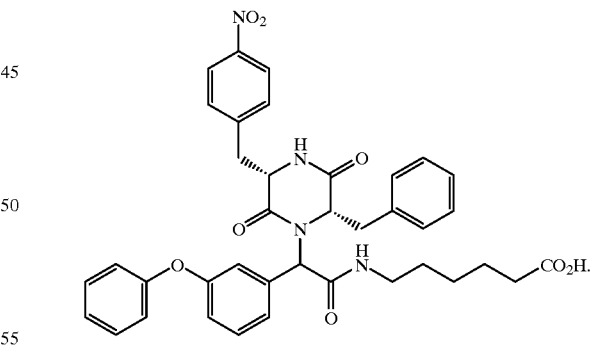

19. A compound by the name of 2-[3-(4-hydroxy-benzyl)-1,4-dioxo-1,3,4,6,11,11a-hexahydro-pyrazino[1,2-b]isoquinolin-2-yl]-N-[2-(4-hydroxy-phenyl)-ethyl]-acetamide having the following structural formula:

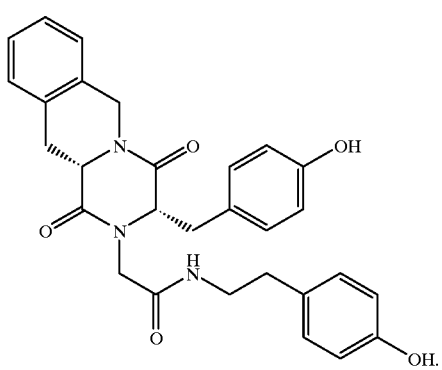
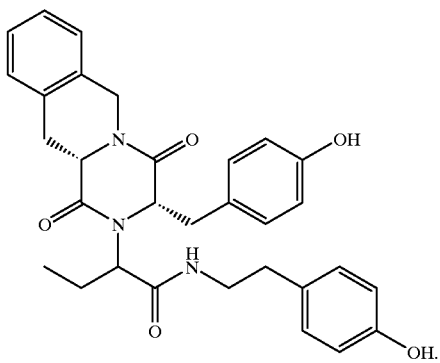

20. A compound by the name of 2-[3-(4-hydroxy-benzyl)-1,4-dioxo-1,3,4,6,11,11a-hexahydro-pyrazino[1,2-b]isoquinolin-2-yl]-N-[2-(4-hydroxy-phenyl)-ethyl]-butyramide having the following structural formula:

21. A method for treating Type-II diabetes in a subject, which comprises the administration of an effective antihyperglycemic amount of a compound selected from those defined in claim 1 or the pharmaceutically acceptable salt or ester therof.

* * * * *